(12) United States Patent
Zhu et al.

(10) Patent No.: US 7,589,122 B2
(45) Date of Patent: Sep. 15, 2009

(54) METHOD FOR SOYBEAN APHID POPULATION SUPPRESSION AND MONITORING USING APHID- AND HOST-PLANT-ASSOCIATED SEMIOCHEMICAL COMPOSITIONS

(75) Inventors: Junwei Zhu, Ames, IA (US); Thomas Baker, State College, PA (US)

(73) Assignee: MSTRS Technologies, Inc., Ames, IA (US)

( * ) Notice: Subject to any disclaimer, the term of this patent is extended or adjusted under 35 U.S.C. 154(b) by 633 days.

(21) Appl. No.: 11/123,668

(22) Filed: May 6, 2005

(65) Prior Publication Data
US 2005/0249769 A1 Nov. 10, 2005

Related U.S. Application Data

(60) Provisional application No. 60/568,640, filed on May 6, 2004.

(51) Int. Cl.
*A01N 43/16* (2006.01)
*A01N 25/00* (2006.01)
*A61K 31/34* (2006.01)

(52) U.S. Cl. .................. 514/469; 514/457; 424/405

(58) Field of Classification Search .............. 504/116.1; 424/405; 514/457, 469
See application file for complete search history.

(56) References Cited

U.S. PATENT DOCUMENTS

| | | | |
|---|---|---|---|
| 4,925,657 A | 5/1990 | Braber et al. .................. 424/45 |
| 5,308,613 A * | 5/1994 | Banfield ....................... 424/84 |
| 6,051,612 A | 4/2000 | Borden et al. ................ 514/693 |
| 6,074,634 A | 6/2000 | Lopez et al. ................... 424/84 |
| 6,217,891 B1 | 4/2001 | Borden et al. ................ 424/405 |
| 6,440,406 B1 | 8/2002 | Lopez et al. ................... 424/84 |
| 6,562,332 B2 | 5/2003 | Baker et al. ................... 424/84 |
| 6,858,653 B1 | 2/2005 | Bessette ...................... 514/730 |
| 2001/0043937 A1* | 11/2001 | Baker et al. ................. 424/405 |
| 2002/0107287 A1 | 8/2002 | Bessette et al. ............. 514/532 |
| 2003/0036530 A1 | 2/2003 | Bessette ....................... 514/65 |
| 2003/0039674 A1 | 2/2003 | Bessette ..................... 424/405 |
| 2003/0068352 A1 | 4/2003 | Dickens et al. .............. 424/405 |
| 2003/0091661 A1 | 5/2003 | Bessette ..................... 424/745 |

FOREIGN PATENT DOCUMENTS

| CN | 1228258 | 9/1999 |
|---|---|---|
| EP | 266822 | 5/1988 |
| GB | 258953 | 7/1925 |
| HU | 49787 | 11/1989 |
| WO | WO9956548 | 11/1999 |
| WO | WO2004028256 | 4/2004 |
| WO | WO2004052101 | 6/2004 |

OTHER PUBLICATIONS

Han, B.Y. et al., Composition of the Volatiles from Intact and Mechanically Pierced Tea Aphid-Tea Shoot Complexes and Their Attraction of Natural Enemies of the Tea Aphid, 2002, Journal of Agricultural and Food Chemistry, vol. 50, pp. 2571-2575.*
Zhu et al. Journal of Chemical Ecology (1999) vol. 25(5): 1163-1177.
Zhu et al. Journal of Chemical Ecology (2005) vol. 31 No. 8: 1733-1745.
James, D. Environmental Entomology (2003) 32(5): 977-982.
James, D. Journal of Chemical Ecology (2003) 29(7): 1601-1609.
Pickett, J. et al. British Crop Protection Conference—Pests & diseases, Proceedings (1984) (1): 247-254.
Aldrich, J. et al. Environmental Entomology (1984) 13(4): 1031-1036.
Dicke, M. et al. J. Chem. Ecol. vol. 16 (2), Accession No. 1990:232528 (1990) 381-396.
Hedine, P.A. et al. J. of the Mississippi Academy of Sciences, vol. 44, Accession No. 90:67108 (1988) 59-66.
Ter-Simonyan, L.G. et al. Zashch. Rast. vol. 5 (Russia) Accession No. 1982:402238 (1982) 48-49.
Ushchekov, A.T., Zashchita Rastenii, No. 8 (Russia) Accession No. 78:26370 (1977) 32.
James, D. Journal of Chemical Ecology (2004) 30(8): 1613-1628.
James, D. Proceedings—BCPC International Congress: Crop Science & Technology, Glasgow, United Kingdom, Nov. 10-12, 2003 (2): 1217-1222.

(Continued)

*Primary Examiner*—Johann R Richter
*Assistant Examiner*—Andriae M Holt
(74) *Attorney, Agent, or Firm*—Patricia Sweeney

(57) ABSTRACT

Soybean volatile compounds, soybean aphid-induced volatile compounds and soybean aphid sex pheromones are semiochemicals of the invention used to suppress soybean aphid population. Methyl salicylate is an embodiment of a soybean aphid-induced volatile compound useful in the invention. Benzaldehyde is an embodiment of a soybean host plant volatile compound useful in the invention. Also useful as sex pheromones are nepetalactol and nepetalactone. The compounds may be blended in a preferred embodiment.

7 Claims, 18 Drawing Sheets

OTHER PUBLICATIONS

James, D. Journal of Chemical Ecology (2005) 31(3): 481-495.
Kobayashi et al. 1st Japan/USA Symp on IPM Tsukuba (Japan) Sep. 29-30, 1981.
Losel et al. Pestic. Sci. (1996) 48: 293-303.
Losel et al. Entomologia Experimentalis et Applicata (1996) 80:79-82.
Marsh, D. J. Ent. (1975) 50(1): 43-64.
Obrycki et al. Annu. Rev. Entomol. (1998) 43:295-321.
New, T.R. Trans. R. ent. Soc. Lond. (1975) 127(2): 115-140.
Soybean Aphid Workshop, University of Illinois, Feb. 5, 2004, Ken Ostile "Soybean Aphids in Minnesota" power point presentation.
Pettersson, J. Entomol. Scand. (1970) 1:63-73.
Pettersson, J. Entomol. Scand. (1971) 2:81-93.
Pickett et al. Annu. Rev. Entomol. (1992) 37:67-90.
Rutledge et al. Annals Ent. Soc. Amer.(2004) vol. 97(2): 241-248.
Sanders, C.J. 1997. Mechanisms of mating disruption in moths, pp. 333-346. in Insect Pheromone Research New Direction. Eds. Cardé, R.T. and Minks, A.K. Chapman & Hall.
Smit et al. Crop Protection (2001) 20: 643-651.
Soybean aphid match 2005. http://www.planthealth.info/soyaphid.htm.
Staten et al. Successful area-wide program to control pink bollworm by mating disruption. In "Pheromone Research: New Directions" R. T. Cardé and A. K. Minks (eds.) Chapman and Hall, New York. pp. 383-396, Mar. 1994.
Voegtlin et al. Ann. Entomol. Soc. Am .(2004) 97:233-234.
Voegtlin, D.J. and Steffey, K. 2004. The soybean aphid in North America: Background and Biology. Midwest States Soybean Aphid Management Workshop, Feb. 5, 2004.
Anderson et al.1987. Sensory system, pp. 153-162. in "Aphids : their biology, natural enemies, and control" edited by A.K. Minks and P. Harrewijn. Amsterdam. Elsevier.
Baker et al. 1990. Use of pink bollworm pheromone in the southwestern United States. In "Behavior-Modifying Chemicals for Insect Management," R. Ridgway, R.M. Silverstein and May Inscoe (eds.). Marcel Dekker, Inc., New York, pp. 417-436.
Baker et al. 1997. A novel controlled-release device for disrupting sex pheromone communication in moths, pp. 141-149. in Technology transfer in mating disruption, Eds. P.Witzgall and H. Arn. IOBC wprs Bulletin, vol. 20, Montpellier, France.
Baker et al. 1998. Widely-spaced, high-emission-rate pheromone sources suppress mating of European corn borer females. In. Zalucki, M. P., R. A. I. Drew, and G. G. White (eds.) Pest Management, Future Challenges. Proc. Sixth Australasian Applied Entomological Research Conference. University of Queensland Printery. pp. 279-288.
Boo et al. Journal of chemical Ecology (2000) Vo. 26, No. 3: 601-609.
Campbell et al. Journal of Chemical Ecology (1990) vol. 16, No. 12: 3455-3465, May 27, 2009.
Canard, M., Séméria, Y., and New, T.R. 1984. Biology of Chrysopidae, pp. 294, Dr W. Junk Publishers, The Hague/Boston/Lancaster.
Chicago Tribune—Knight Ridder/Tribune Business News. 2003. Soybean aphids drain production of Midwestern cash crops. Oct. 11, 2003.
CNN News (Associated Press). 2003. Aphids whittling soybean farmers' profits. Nov. 25, 2003.
Cullen, E. 2004. Soybean aphid-Wisconsin 2003 Recap. Midwest States Soybean Aphid Management Workshop, Feb. 5, 2004.
Du, Y-J. Acata. Entomol. Sinica.(1995) 37:385-391.
Frazer, B.D. 1988. Coccinellidae. in Aphids-Their Biology, Natural Enemies and Control. (A.K. Minks, P. Harrewijn, eds.), vol. B, pp. 231-247. New York, Amsterdam: Elsevier.
Gerling, D.1990. Natural enemies of white flies: predators and parasitoids. In Whiteflies: Their Bionomics, Pest Status and Management. (D. Gerling, ed.), pp. 147-185. Andover: Intercept Ltd.
Hardie et al. Chemoecology (1992) 3:113-117.
Hardie et al. Physiological Entomology (1996) 21: 97-106.
Eisenbach et al. Insect Physiol. (1980) vol. 26: 511-515.

* cited by examiner (4aS,7S,7aR)-Nepetalactone (1R,4aS,7S,7aR)-Nepetalactol

METHOD FOR SOYBEAN APHID POPULATION SUPPRESSION AND MONITORING USING APHID- AND HOST-PLANT-ASSOCIATED SEMIOCHEMICAL COMPOSITIONS

CROSS-REFERENCE TO RELATED APPLICATIONS

This application claims priority to a previously-filed application, U.S. Ser. No. 60/568,640, filed May 6, 2004, the contents of which are incorporated herein by reference. All references cited herein are also incorporated herein by reference

REFERENCE TO GOVERNMENT FUNDING

This application is directed to work funded by the National Science Foundation SBIR program (Grant No. 0319092 and 0450032); the United States government may have certain rights in the invention.

FIELD OF THE INVENTION

This invention relates to the use of insect behavior-modifying chemicals (semiochemicals) to manipulate the behavior of the soybean aphid, *Aphis glycines*, and its insect predators, in order to suppress soybean aphid populations or to monitor their densities. The invention is to use of newly identified soybean aphid sex pheromone components and host-plant-associated semiochemicals affecting the soybean aphid and its predators, for directly suppressing soybean aphid populations as well as for monitoring their abundance, thereby reducing damage to economically important U.S. crops.

BACKGROUND OF THE INVENTION

The soybean aphid, *Aphis glycines* Matsumura, is a newly invasive insect species that seriously threatens U.S. soybean production. It is the only aphid species to develop large colonies on soybeans, *Glycine max*, in North America. Since its first appearance in Wisconsin, it has spread to over 20 states in the U.S. and three provinces in Canada (Soybean Aphid Watch 2005). Infestations of this pest whittle soybean growers' profits and cause hundreds of millions of dollars in losses (CNN News, Nov. 25, 2003; Chicago Tribune Business News, Oct. 11, 2003). In 2003, the total acreage having soybean aphid infestations was estimated at over 8 million acres, with yield losses ranging from 32%-45% from the three biggest soybean-growing states (data digested from research conducted in Illinois, Iowa and Minnesota and reported at the Midwest Soybean Aphid Workshop, Feb. 5, 2004).

The soybean aphid is originally a native of China and Japan, and until recently, mainly occurred only in several Asian countries, Australia, and on several Pacific islands. It has a complex life cycle with more than 15 generations annually. Two different types of host plants are necessary for the completion of its life cycle. In Iowa, winter survival of overwintering eggs occurs on the aphid's primary host, the common buckthorn, *Rhamnus cathartica*. However, winged females (called 'gynoparae') are also found on the leaves of another *Rhamnus* species (*R. alnifolia*) in other north central states (Voegtlin et al., 2004). The gynoparae produce a generation of wingless pheromone-emitting females (called "oviparae") in late fall on buckthorn. This is the only sexually reproducing generation, and the only one in which sex pheromones are used for mating. The overwintering eggs from these wingless females that mate with winged males in the fall result in the first winged generation (alate viviparous female) that take flight early in the spring. These females migrate from buckthorn in search of soybeans, *Glycine max*, the secondary host plant. On soybeans, a series of wingless generations (apterous viviparous females) are produced, which are followed by a winged generation that disperses from infested soybean plants in search of other less-infested soybean plants. During the fall, winged females (gynoparae) fly back to the common buckthorn to produce a new generation of pheromone-producing oviparae. Males that develop late in the season on soybeans search for buckthorn and mate with oviparae, which lay the overwintering eggs on buckthorn twigs (See FIG. 1, diagram of the soybean aphid life cycle).

Application of insecticides has been the first approach to suppress this pest species during the growing season, but there are the usual risks that beneficial insects will be killed or repelled and that the environment can become polluted. Furthermore, insecticides may not be entirely effective, and populations of soybean aphids do tend to rebound after insecticide application by developing resistance quickly (Cullen, 2004; Ostlie, 2004). The insecticides labeled for soybean aphid management listed in Table 1 are all restricted from use within at least 20 days of harvesting by the EPA; this is the most critical period of the life cycle, during which the overwintering population is generated. Further results from soybean aphid suction traps during the fall of 2002 have shown that the higher density fall population in 2002 contributed to the most serious soybean aphid infestation during 2003 since the arrival of this in the U.S. (Voegtlin and Steffey, 2004).

TABLE 1

Insecticides Labeled for Soybean Aphid Control

| Insecticide | Rate (fl oz/acre) | Post Harvest Restriction (day) | Class |
| --- | --- | --- | --- |
| Asana XL | 5.8-9.6 | 21 | Pyrethriod |
| Baythroid 2E | 2.8 | 45 | Pyrethriod |
| Dimethoate | 16 | 21 | Organophosphate |
| Furadan 4F | 8 | 21 | Carbamate |
| Lorsban 4E | 16-32 | 28 | Organophosphate |
| Mustang Max | 3.4-4.3 | 21 | Pyrethriod |
| Penncap-M | 32-48 | 20 | Organophosphate |
| Pounce 3.2EC | 4-8 | 60 | Pyrethriod |
| Warrior T | 1.92-3.84 | 45 | Pyrethriod |

During the growing season, soybean aphids are attacked by a variety of insect predators and parasitoids. The complex of these natural enemies plays a potential key role in regulating soybean aphid populations. Field observations in soybean fields indicate that *Coccinella septempunctata* dominates early in the season with an increasing abundance of *Harmonia axyridis* and *Coleomegilla maculata* as the season progresses. The most common lacewing species, *Chrysoperla carnea*, also flies during the soybean growing season, and their larvae have been observed attacking soybean aphids. There is also an abundance of larvae of syrphid flies preying on soybean aphids. We documented a second lacewing species, *Chrysopa oculata*, flying in the late fall when gynoparae and sexually active male and female soybean aphids occur. These lacewings are predacious during both the adult and larval stages. The inventors here isolated and identified several plant-related volatile compounds that attract the adults of several species of predaceous insects (Zhu et al., 2005; Zhu and Park, 2005).

The use of predaceous insects, including coccinellids, chrysopids and other predatory insects, as biological control agents to suppress population of pest species on economically important agricultural crops or in home gardens, is widely accepted and recognized by the general public and by biological control practitioners (see references in, Obrycki and Kring, 1998; Canard, et al 1984). There have been significant successes in using such insects to suppress whitefly, aphid, mealybug, scale and mite populations (Gerling, 1990; Frazier, 1988; New, 1975). Despite the significant success of employing these two groups of predatory insects for biological control, two of the most important factors impacting the effectiveness of biological control are the timing of the abundance of predatory insects on targeted pests and the dispersal behavior of many predaceous species (Frazier, 1988; Rutledge et al. 2004). The use of attractants of predatory insects of soybean aphids offers significant potential to manipulate these beneficial insects in aphid-infested habitats (Zhu et al., 1999; Zhu et al., 2005; Zhu and Park, 2005).

During the fall, gynoparae fly from soybean fields to locate their winter host plants, where they give birth to live, wingless, sexually-active females (oviparae). These females are the only sexually reproducing females during the entire year. The mature oviparae emit a sex pheromone that attracts winged males from the same generation that produced the gynoparae; these males have also flown out of soybean fields to locate buckthorn plants. The eggs resulting from mated oviparae are laid on buckthorn for overwintering. The sex pheromone is released from glandular cells on the tibiae of the hind legs; this communication system has been demonstrated in several aphid species (Pettersson, 1970 and 1971, Pickett et al., 1992).

The sex pheromones of several aphid species that have been identified thus far (Picket et al., 1992; Boo et al., 2000) all involve compounds derived from the catmint plant, *Nepata cataria*. These include two compounds, (1R,4aS,7S,7aR)-nepetalactol (nepetalactol) and (4aS,7S,7aR)-nepetalactone (nepetalactone), the precise blend of which we determined specifically attracts both spring alatae and males and gynoparous soybean aphids (Zhu et al., submitted).

The aphid olfactory receptor system shows a great abundance of organs called secondary rhinaria that are located on the antenna of the alate morphs. The majority of these rhinaria are flat, plate-like organs (placoid sensilla) (Anderson and Bromley, 1987), which suggests their involvement in host plant location and mate finding (Eisenbach and Mittler, 1980; Marsh, 1975; Pettersson, 1971). In soybean aphids, Du et al. (1995) reported that the olfactory systems of soybean aphid males and gynoparous females are quite similar with regard to the abundance of placoid sensilla found on their antennae.

The use of synthetic sex pheromone to disrupt mating behavior has become a widely accepted and increasingly used IPM tool for suppressing populations of several key lepidopteran pests of agricultural crops and tree fruits around the world (Baker and Heath, 2004; Baker et al., 1997; Sanders, 1997). These disruption systems have resulted in a significant reduction in the number of insecticide applications (Baker and Heath, 2004; Staten et al., 1990; Baker et al., 1990). Earlier reports have suggested that the active range of male aphids responding to female sex pheromone is relatively short, which could be problematic when developing mating disruption techniques against aphid pests. However, recent studies have shown that males of several aphid species can be selectively attracted to traps releasing synthetic aphid pheromones at relatively long distances, as can gynoparous female aphids be attracted to host plant associated volatiles (Campbell et al., 1990; Hardie et al., 1992; 1996; Boo et al., 2000; Lösel et al., 1996a, b). These recent findings are encouraging for the potential deployment of aphid mating disruption technique using sex pheromones.

Another integrated pest management (IPM) component, mass trapping of insect pests using sex pheromones or host plant volatiles, has also shown renewed promise as a population management tool (Kobayashi et al., 1981; Smit et al., 2001) for both moth and beetle pests (Baker and Heath, 2004). Mass trapping of male soybean aphids as they leave soybean fields to locate females on the winter host, by using inexpensive traps placed in soybean fields, may be a feasible approach to explore. Likewise, mass trapping of gynoparae leaving soybean fields may reduce population densities of overwintering aphids.

There is a particular need to identify such compounds for use in suppressing and impacting soybean aphid populations, a pest causing economic damage.

SUMMARY OF THE INVENTION

The invention is to utilize plant-derived semiochemicals, including both the catmint-plant-derived soybean aphid sex pheromone blend as well as plant-associated predatory insect attractants, to suppress soybean aphid populations directly or by using these compounds combined in monitoring traps.

In one embodiment, the semiochemicals are plant volatile compounds including aphid-feeding-induced plant-emitted volatile compounds that can be used in suppressing aphid populations. In a preferred embodiment these compounds include (E)-2 hexenal, (Z)-3 Hexenol, benzaldehyde, (Z)-3 hexenyl acetate, linalool, 6-methyl-5-hepten-2-one, ocimine, 2-phenylethanol, (E,E)-α-farnesene, and methyl salicylate. In a preferred embodiment these compounds include the induced plant aphid-feeding-induced plant-emitted volatile compound of methyl salicylate. In an embodiment of the invention, the composition deployed into a target comprises a range of effective doses from 10 mg to 300 mg when the volatile is methyl salicylate.

In another embodiment, the semiochemicals, sex pheromones, neptalactol or neptalactone are used to suppress aphid populations. In a preferred embodiment, the amount of neptalactol or neptalactone released in the target area is 0.1 mg to 50 mg in a 24 hour period. In still another embodiment, the nepetalactone and neptalactol is combined, and in a still further preferred embodiment, the nepetalactol comprises at least about 10% of the composition. In a preferred embodiment this blend consists of a ratio of 35:65 nepetalactol to nepetalactone.

A blend of the any of above semiochemicals may be used which combines at least one or more of any of the host plant volatiles and/or sex pheromones. Either the host plant volatiles, or the soybean aphid sex pheromones, or a combination, may be used to suppress their populations, to disrupt the mating of soybean aphids, to suppress their success of the overwintering populations, or mass-trap soybean aphids. In another embodiment, the aphid-induced host plant volatile compounds methyl salicylate or (E,E)-α-farnese are used to attract insects predatory to soybean aphids.

In another embodiment the soybean aphid sex pheromone, or soybean volatile compound, or combination, is used in monitoring traps to indicate population levels that can be suppressed by the application of insecticides or by other means. In one embodiment the volatile benzaldehyde is used. In an embodiment this blend consists of a blend of nepetalactol to nepetalactone mentioned above, or benzaldehyde, or the three combined.

The invention also provides compositions comprising effective dosages of soybean aphid and host-related volatiles, suitable dispenser systems for emitting these compounds, and trapping/trappant systems for use in both monitoring and in mass trapping and mating disruption.

DETAILED DESCRIPTION OF THE INVENTION

Figure 1:
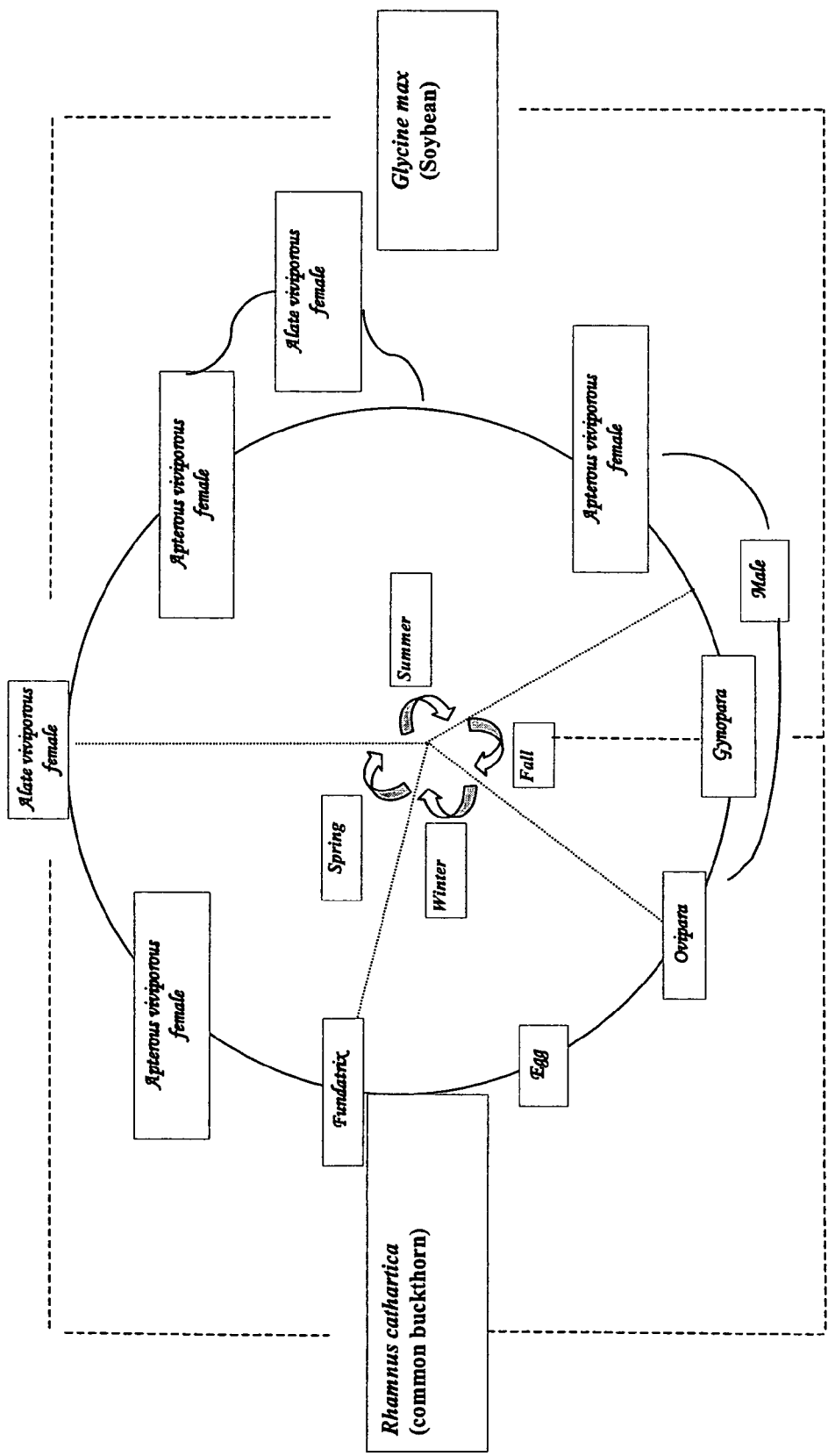
FIG. 1 is a representation of the life cycle of the soybean aphid.

The invention describes methods to use attractant compositions, including semiochemicals such as soybean aphid sex pheromone components and host-plant-associated volatiles, to behaviorally manipulate the soybean aphid and its predators to suppress soybean aphid populations as well as to monitor the aphids' abundance. Further, the invention is to a blend of more than one volatile, a blend of more than one soybean aphid-induced volatiles, and/or a combination of the volatiles and soybean aphid induced volatiles. In yet another embodiment, the blends or combinations can be further combined with one or more soybean aphid sex pheromones.

The invention provides several innovative and environmentally benign biologically based pest management approaches, such as mass trapping and mating disruption of the soybean aphid's fall generation and also the monitoring and prediction of soybean aphid movement and outbreaks using the soybean aphid sex pheromone. The invention also provides novel methods for attracting insects that are predaceous upon soybean aphids to target soybean-aphid-infested areas using compositions of soybean plant volatiles, thereby enhancing biological control. In particular, given the adverse economic impact on soybean crops in particular, the development of this system against soybean aphids will give soybean farmers in North America a new tool against this pest, and may especially be helpful to growers of organic soybeans who currently have no means of non-insecticidal population suppression against this pest.

The following definitions are used, unless otherwise described.

"Attract" refers to causing an insect to displace toward the source of a chemical composition.

"Attractant" refers to any chemical composition that causes, either directly or indirectly, an insect to displace toward the source of the chemical composition. A chemical composition causing attraction can be an individual compound or a composition, including more than one compound, which either directly or indirectly, such as initiating an optomotor program of steering into the wind, causes the insect to displace toward the source of the chemical composition.

"Repellent" refers to any chemical composition that causes, either directly or indirectly, an insect to displace away from the source of the chemical composition. A chemical repellent can be an individual compound or a composition, including more than one compound, which either directly or indirectly, such as initiating an optomotor program of steering down-wind, causes the insect to displace away from the source of the chemical composition.

"Predatory Insects" refers to those insects that prey upon aphids infesting plants. By way of example without limitation, such predatory insects include members of the family Coccinellidae (lady beetles), Syrphidae (syrphids), Chrysopidae (lacewings), and Anthocoridae (true bugs). Further specific examples include, and are not limited to, *Coccinella septempunctata, Syrphus* sp, *Chrysopa oculata* and *Orius insidious* (Say).

"Applying" and "Application" includes any suitable method of emitting an effective dose of the semiochemical to an area. By way of example, without limitation, is included the broadcast or restricted localized spraying of a volatile in or around an area, with or without first microencapsulating the volatile, emitting the volatile from one or more controlled-emission point-source dispensers placed in or around an area, and integrating the release of the volatile with an irrigation technique ("chemigation").

"Dispenser" refers to any device that disperses the semiochemicals. "Controlled-emission point-source dispenser" refers to any suitable method for controlling the emission rate of the volatile compound from a concentrated source reservoir of the compounds. Such methods include, but not limited to: pads, beads, rods, spirals, or balls comprised of rubber, leather, cotton, wood, glass or wood products, polyethylene, polypropylene or polyvinyl chloride that are impregnated with the volatile compounds, micro-capillary tubes open at one end; sealed polyethylene or polypropylene tubes sealed at both ends; laminates comprised of layers of the volatile compound alternated with plastic and cut in various sized flasks or preserved as large ribbons or sheets; permeable or semi-permeable membranes covering a non-permeable container serving as a reservoir for the volatile compounds; large porous beads or sponges; micro-capsules; sealed envelopes or bags made of polyethylene, polypropylene, paper, or other permeable substances, metered aerosol systems utilizing pump or pressure technologies to emit aerosolized droplets of the volatiles into the atmosphere, onto plant surface or dirt, or onto any of above controlled-release point-source dispensers; and non-aerosol micro-pump technologies that cause metered quantities of the compounds to be dispensed and volatilized by any of the above methods. When referring to "traps" any means of trapping an insect is included, such as adjustable pan traps, sticky traps and the like.

"Target area" includes any place where the presence of the semiochemicals of the invention is desirable to achieve suppression, attraction, monitoring, trapping or the like of soybean aphids, and/or attraction of their predators, such as, for example, a farm field, a garden, or a horticultural or floricultural nursery.

"Semiochemicals" refers to naturally occurring biochemical signals used by insects, plants, and other organisms for communication with other organisms in their environment and includes plant volatile compounds insect-feeding-induced plant volatile compounds and insect sex pheromones, among others.

"Volatile" refers to compounds, compositions, or mixtures with a sufficient vapor pressure so that at least some of the matter can be readily vaporized at ambient temperature or temperatures slightly above ambient, and the resulting vapors can be detected and responded to by, for example, the living insect, or the insect's extirpated antenna.

"Odor" refers to an individual compound, a composition of volatile compounds, or a specific blend ratio of two or more volatile chemicals.

The semiochemicals of the invention are plant-produced and soybean aphid-produced volatile compounds to be used to repel or attract target insects. By soybean volatiles is meant those compounds produced by soybeans (*Glycine max*) and include volatiles from their host plants (both primary and secondary host plants of soybean aphids) and their prey host plants, as well as the pheromone of the soybean aphid, *Aphis glycines* (prey associated). Preferred plant volatiles useful in the methods of the invention include general leaf volatiles, terpinoids (monoterpene, sesquiterpene and their corresponding alcohols), and phenolics, such as phenyl alcohols, phenyl esters and phenyl ketones. For example, see Liu, et al., 1989, J. Agri. Food Chem. 37:496-501; Du, et al., 1994, Acta Entomol. Sinica, 37:385-391; Zhu, et al., 2005; Pickett, Wadhams and Woodcock, 1992. Annu. Rev. Entomol. 37:67-90. Preferred compounds include (E)-2 hexenal, (Z)-3 Hexenol, benzaldehyde, (Z)-3 hexenyl acetate, linalool, 6-methyl-5-hepten-2-one, ocimine, 2-phenylethanol, (E,E)-α-farnesene, methyl salicylate and 4aS,7S, 7aR)-nepetalactone and (1R,4aS,7S,7aR)-nepetalactol. Note that when referring to nepetalactone and neptelactol, it is not necessary to use the compounds from any particular source. In fact, experiments discussed below indicate catnip oil can be the source of nepetalactone, and the compound need not be purified. By the term soybean aphid induced volatiles, is meant the group of soybean volatiles which are produced by healthy soybean leaves, or when the aphid ingests, damages, or otherwise attacks the soybean, the volatiles are produced under latter circumstance by the plant as a defensive mechanism. An example of such a compound is methyl salicylate and (E,E)-α-farnesene. Sex pheromones are those semiochemicals used by members of the opposite sexes of the same species for sexual communication, and here sex pheromones are those used for communication for purposes of insect reproduction. By way of example, without limitation, a preferred pheromone that can be used in the invention, is a sex pheromone components of the soybean aphid, (4aS,7S,7aR)-nepetalactone and/or (1R,4aS,7S,7aR)-nepetalactol. The pheromones can be blended together, or blended with other pheromones or host plant volatiles. One skilled appreciates that a blend of any of the semiochemicals can be formulated, including blends with other desirable compounds. The compounds can be formulated to dispensers for pheromone mating disruption and mass trapping during the fall for suppressing their overwintering population.

The inventors have discovered that semiochemicals, including volatile plant compounds, soybean aphid induced volatile host plant compounds and soybean aphid sex pheromone compounds, separately or together, can be used to in monitoring the outbreaks and to assist timing the application of pesticides, or other means of reducing aphid damage. For example, the volatiles can be used to attract predatory insects that prey soybean aphids. The compositions and methods of the invention can be used to attract adult predatory insects to any area where their presence may be desired. The adults of female and male predatory insects can themselves consume the prey, as well be afforded increased probability of locating mates and laying eggs; their subsequent larval offspring will also prey on the aphids. In addition, the attraction of soybean aphids can also be used as an indicator for predicting the outbreak of soybean aphids during the spring. The soybean-aphid feeding-induced emission of volatiles from the plants has also been shown to decrease infestations; the aphids' propensity to avoid such compounds results in reduced populations.

Optimal amounts of semiochemicals needed to evoke attraction (attractive amounts) or aphid avoidance of plants (repellency) will depend on the application technique employed and on the specific conditions of the area at the time of application. From the controlled-release point-source dispensers the reservoir amounts will typically be about 10 mg or higher, and the release rates will be 10 ng/min or higher.

In preferred embodiments of the invention, the amount of methyl salicylate from a dispenser comprises about 10 mg to 300 mg of methyl salicylate. When neptalactone or neptalatol is used in the composition, a preferred amount released from a dispenser comprises about 1 mg to about 50 mg/day (mating disruption). A further preferred amount is 0.1 mg to 5 mg/day (mass trapping). When blending nepetalactol with nepetalactone, it is preferred the nepetalactol is at least about 10% of the composition. Another embodiment provides the nepetalactol and nepetalactone at a ration of 35:65.

The following is presented by way of illustration and is not intended to limit the scope of the invention.

EXAMPLE 1

Materials and Methods

Plants and insects. V1 and V2 stage Soybean plants (*Glycine max*), Garst Roundup Ready, variety. 80411203, greenhouse grown in small pots, were used when for infestation and entrainment. This stage of soybean plants was also reported when spring winged aphids started to emigrate from their overwintering host plant, buckthorn (*Rhamnus cathartica*) to the soybean. Soybean aphids collected from soybean fields at the University Farms (Ames, Iowa), were maintained in the laboratory in a cabinet maintained at 25±2° C., with a light cycle of 14 hrs: 10 hrs, L: D., as a stock colony with only parthenogenetically produced females. Adults of *C. septempunctata* were collected from soybean fields during early summer, and maintained in the same condition as described for soybean aphid colony, with only sugar water (5%) provided.

Volatile collection from soybean aphid-infested and undamaged soybean leaves. The collection apparatus for volatile compounds comprised two glass half-cells (9.5 cm ID×12 cm deep and 10 cm ID and 15 cm deep), which when put together formed a chamber around the plant with the stem passing through a small slit. The remaining space around the slit was packed with glass wool, held in place with Teflon tape. The moisturized and charcoal filtered air was pumped into the chamber through the inlet, and the outlet of the chamber was connected with a pre-baked (200° C. over night) glass tube (5 cm×0.3 cm ID) containing 100 mg of Super Q (80/100 mesh, ALLTECH Associate, Deerfield, Ill.) sandwiched with glass wool plugs. An air flow rate was measured around 400 ml/min from the Super Q collector using a HP digital flow meter. The entrainment was carried under the same condition as described for soybean growth.

Volatile entrainment was conducted from V1 and V2 stage of soybean plants. 30 $2^{nd}$ instar soybean aphids were transferred on leaves of one soybean plant, and collection was started after 6 hours of introducing. A control plant (same stage) was set up in exactly the same way but without the aphids. Volatiles were collected every other day from the first day to $12^{th}$ day. Volatile collection from only soybean aphids was also conducted in a 12 oz wide mouth glass bottle with around 200 soybean aphids (2-3 instar) with the same method described above. The trapped volatiles were eluted with 2 ml of HPLC-grade hexane (Burdick & Jackson Brand™ High Purity) containing 250 ng of pentadecane as an internal standard, and then concentrated to 200 µl under a gentle nitrogen stream. Two µl of extracts were injected into either combined gas chromatography and electroantennographic detection (GC-EAD) or gas chromatography—mass spectrometry (GC-MS) for quantitative and qualitative analyses.

Inducing pheromone producing female and responding male soybean aphids. The aphids are collected from local soybean fields (Ames, Iowa) and are raised on potted soybean plants. They are initially kept in a growth chamber maintained at 25±2° C. as a stock colony with only parthenogenetic females produced. To induce sexual forms of soybean aphids to occur in the lab, 10 winged or non-winged asexual females are transferred and reared on a soybean plant under fluctuating photoperiod and temperature programs as described above that mimic conditions during the late fall in the Upper Midwest. The progeny from these aphids are checked every week, and segregated according to age throughout the next 4-5 weeks until winged males emerge, indicating also that the winged females that emerge are of the sexually reproducing type. During the last week of the induction, common buckthorn leaves are provided for these females to feed on, which then promotes the biosynthesis and emission of sex pheromone by these females. The induced male and female soybean aphids were separated and rearing in two different 16 oz bottles for used in experiments.

Pheromone collection. Two methods, solvent extraction and air entrainment, will be used for collecting putative sex pheromone components from pheromone-emitting females (oviparae). For the solvent extraction method, 20 hind legs of oviparae will be dissected, and extracted with 20 µl of diethyl ether. The dissections will be performed on oviparae at three different times during the photoperiod, 0-3 hr, 3-6 hr and 6-9 hr while they are observed calling. To get the precise airborne released pheromone, the air entrainment method will be deployed. Thirty mature oviparae maintained on leaves of the common buckthorn with ends of the cut branches held in a water-filled test tube, will be placed in a ventilated glass jar (32 oz wide mouth bottle). Activated-charcoal-filtered air will be drawn from the container at a rate of 0.5 liter/min. Volatiles will be entrained onto a adsorbent collector system (a glass tube containing 250 mg of Super Q, 80/100 mesh, ALLTECH). The collection will last from several hours to 2 days, the volatiles then being desorbed by eluting the adsorbent with 3 ml of distilled hexane. The rinsed hexane will be concentrated to a volume of approx. 50 µl for further chemical analytical analyses.

Chemical Analyses. For GC-EAD analysis, a Hewlett Parkard 5890 Series II gas chromatograph equipped with either a DB-5 or a DB-wax column (30 m×0.25 mm i.d., J&W Scientific, Folsom, Calif.), and a 50:50 effluent split allowed simultaneous flame ionization (FID) and EAD of the collected volatiles. Helium was used as the carrier gas with a flow rate of approximately 30 ml/min for both FID and EAD. Extracts were injected in splitless mode. The injector temperature was 250° C., and the split valve was opened 1 min after injection. The temperature program was 50° C. (3 min) to 250° C. at 15° C./min. The outlet for the EAD was continuously supplied with a purified, moisturized air stream flowing over the antennal preparation at 0.5 m/sec. An adult of *C. septempunctata* was restrained on a block of dental wax with thin copper wires (32 Gauge) for EAD recordings. A glass capillary recording Ag—AgCl electrode filled with saline (0.1 M KCl solution) was placed in contact with the distal segment of the antenna. The ground electrode, filled with the same solution, was impaled into the beetle body. The EAD amplifier (a high-impedance DC amplifier and an automatic baseline drift compensation) was purchased from Syntech (Hilversum, The Netherlands). A GC-EAD program (version 2.3) developed by Syntech was used to record and analyze the amplified EAD and FID signals on a PC computer (Micron Inc., Minneapolis).

GC-MS analyses of the volatiles collected from soybean plants and gynoparous soybean aphids were performed with a Hewlett Packard 5890 Series II gas chromatograph interfaced to a Hewlett Packard 5972 Mass Selective Detector (MSD). The GC-MS was equipped with the same columns as used in the GC-EAD system described above. The temperature program was the same as that described for the GC-EAD analyses. Mass spectra were recorded from 30 to 550 a.m.u. with electronic impact ionization at 70 eV. The assignments of chemical identities to the soybean volatile compounds were confirmed by comparison of the retention indices and mass spectra with those of authenticate chemical standards and reference spectra in a mass spectral library (Wiley 138K, John Wiley and Sons, Inc.).

The structures of the MS-identified pheromone compounds were further confirmed by analysis by nuclear magnetic resonance ($^1H$ and $^{13}C$ NMR) spectroscopy.

Chemicals. All synthetic standards of soybean volatile compounds were purchased from Sigma/Aldrich (St. Louis, Mo.), and the purity of each compound was analyzed in GC-MS ranging from 98%-99.5%. Synthetic soybean aphid pheromone compounds were synthesized as described: the (4aS,7S,7aR)-nepetalactone was extracted from catmint plants *Nepeta cataria* (Lamiaceae) by steam distillation. Catmint plants were collected from the University Farms (Ames, Iowa). Cut leaves and stems of catmint were placed into a 2-liter, three-necked boiling flask, then 1 liter of water will be added. The flask was heated to boiling point. The distillate was collected and washed three times with hexane, then hexane was removed by using rotary evaporation at 500 mm Hg vacuum at 25° C. According to results of GC-MS analysis of the distillate from our repellent research project, it contains about 98% of the nepetalactone (4aS,7S,7aR)-nepetalactone and (4aS,7S,7aS)-nepetalactone. The two isomers were separated by using either High pressured liquid chromatography (HPLC) or silica gel preparative thin-layer chromatography plates (TLC). HPLC was conducted using a Hewlett Packard series 1100 HPLC with a Pirkle Covalent Phenylglycine hichrom preparative column (25 cm×10 mm I.D., 5 microns S5NH Modified Spherosorb). A mobile phase of 9:1 hexane: ethyl acetate at about 2.5 ml/min was selected, and detection using a Spectroflow 757 UV-Detector at 254 nm. For separating these two isomers using TLC, TLC plate (20×20 cm, 1,000 µm in thickness, Whatman, Hillsboro, Oreg.) was used with a solvent system of 19:1 hexane/ethyl ether. The products were visualized under 254-nm UV light, and the silica gel was scraped off the plated and washed with ethyl ether. The solvents used by two methods were removed by rotary evaporation, and the purity of the isomer was assessed by analyzing in GC-MS with comparison of authentic aphid compound provided by Dr. Pickett at Rothamsted Experimental Station, UK. The resulting (4aS,7S,7aR)-nepetalactone was reduced to the corresponding (1R,4aS,7S,7aR)-nepetalactol using the diisobutylaluminium hydride (DIBAL-H) reduction of the above purified nepetalactone. The structure of reduction product was finally characterized by $^{13}C$ NMR: peaks at 93.9 p.p.m (—OCHOH), 133.5 and 113.1 (C═CH—O) and 7 others upfield, and by $^1H$ NMR: characteristic peaks at 6.01 p.pm (═CH—O), 4.85 (O—CH—O) and 2.82 (OH), with 5 Hz coupling from the 4.85 peak to both the OH peak and an octet at 1.64 (H-7a) (3). The absolute stereochemistry of the reduced nepetalactol at C-1 will be determined by NMR spectrum (5 Hz coupling between Hs 1 and 7a).

The effect of Methyl salicylate on soybean aphid growth. This experiment was conducted in the green house, where cages of soybean plants treated with dispensers loaded 4 g of synthetic methyl salicylate. Newly emerged winged soybean aphids on one cut-soybean leaf (dried) were placed in the middle of the cage, which is 30 cm away from the potted soybean plants (V2 stage) with or without treatment of methyl salicylate. For plants treated with methyl salicylate, the cotton roll was placed in the center of the plant, and was replaced with a newly loaded one after one week. The number of winged aphids on each plant were counted 2 hours after introducing the winged aphids, and continued for a week. The number of wingless soybean aphids produced from those landed winged aphids was also counted everyday for about two weeks.

Field Test. Field trapping tests were conducted in soybean field from 2002 to 2003 (Ames, Iowa). Synthetic compounds at a dose of 100 mg (for plant volatiles) and 10 mg for soybean aphid pheromones were prepared in either hexane or methylene chloride or ether. Medical peerless cotton rolls (5 cm long, 100% cotton) were used as dispensers for loading plant volatiles, and borosilicate glass vials (Chromal) were housed for pheromones. Two trap designs were used, and the first type is similar to that described in Zhu et al., (1999), and the second one is the most common trap used for aphid trapping, the water trap. The trap was hung from bamboo stakes, 1.2 m above the ground. Within a replicate (N=5-6), traps were set at least 10 m apart. The traps were checked daily, and trap position within a series was randomized to minimize the effects of habitat heterogeneity.

Statistical analyses. The resulting differences in volatile emission among different treatments in the volatile collection experiments and trap catches (means of trapped species) were compared by either Student T-test or analysis of variance followed by Fisher's protected least significant difference test (FPLSD).

Results

Figure 2:
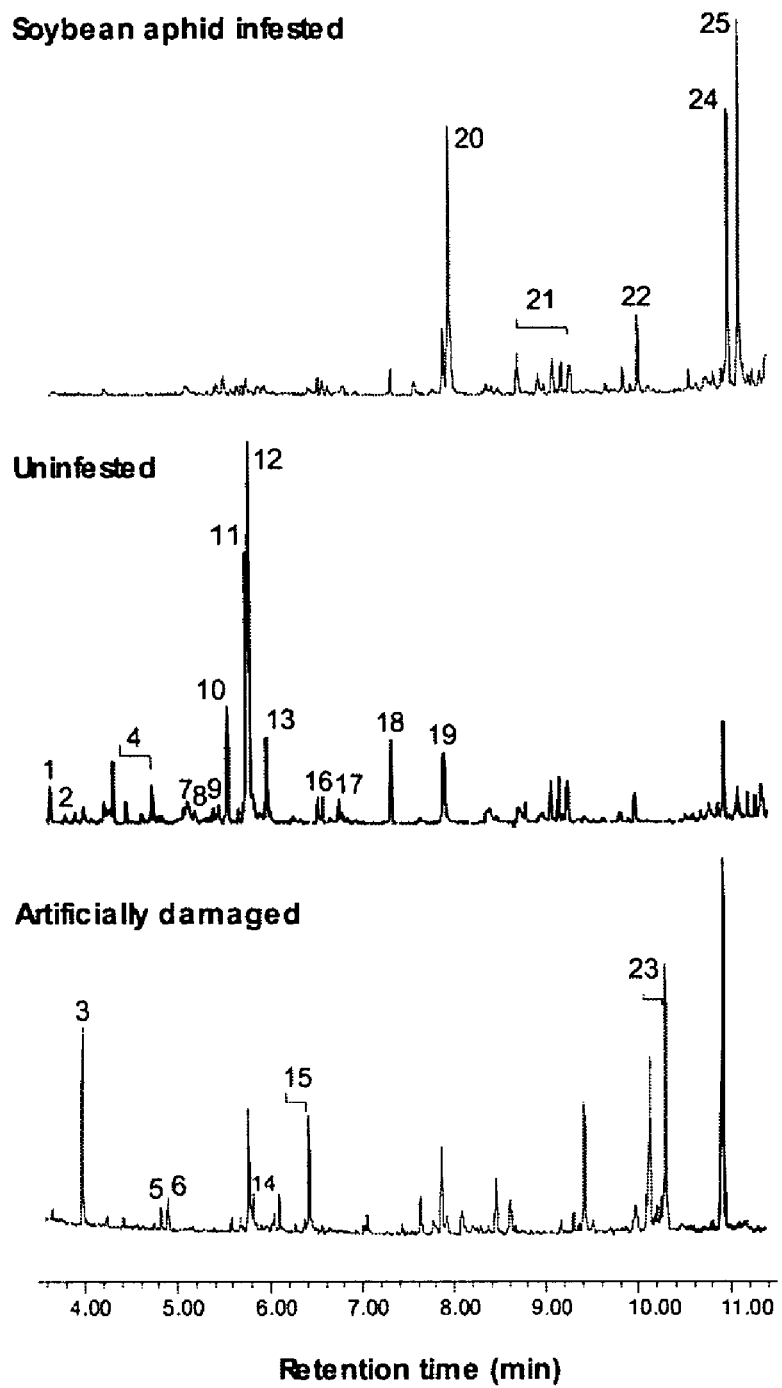
FIG. 2 show graphs of typical gas chromatograms (On a DB-5 column) of volatile compounds emitted from soybean aphid-infested, artificial-damaged and undamaged plants of *Glycine max*. Represented are: 1: E2-hexenal; 2: E2-hexenol; 3: toluene; 4: unknowns; 5: Ethylbenzene; 6: 1,3-dimethyl benzene; 7: benzaldehyde; 8: 6-methyl-5 heptanone; 9: Z3-hexenyl acetate; 10: decane; 11: 1,2,3-trimethyl benzene; 12: dichlorobenzene; 13: D-limonene; 14: ocimene; 15: unknowns; 16: linalool; 17: 2-phenylethanol; 18: unknown; 19: naphathlene; 20: methyl salicylate; 21: unknowns; 22: tetradecane; 23: unknowns; 24: α-humulene; 25: (E,E)-α-farnesene.
Figure 6:
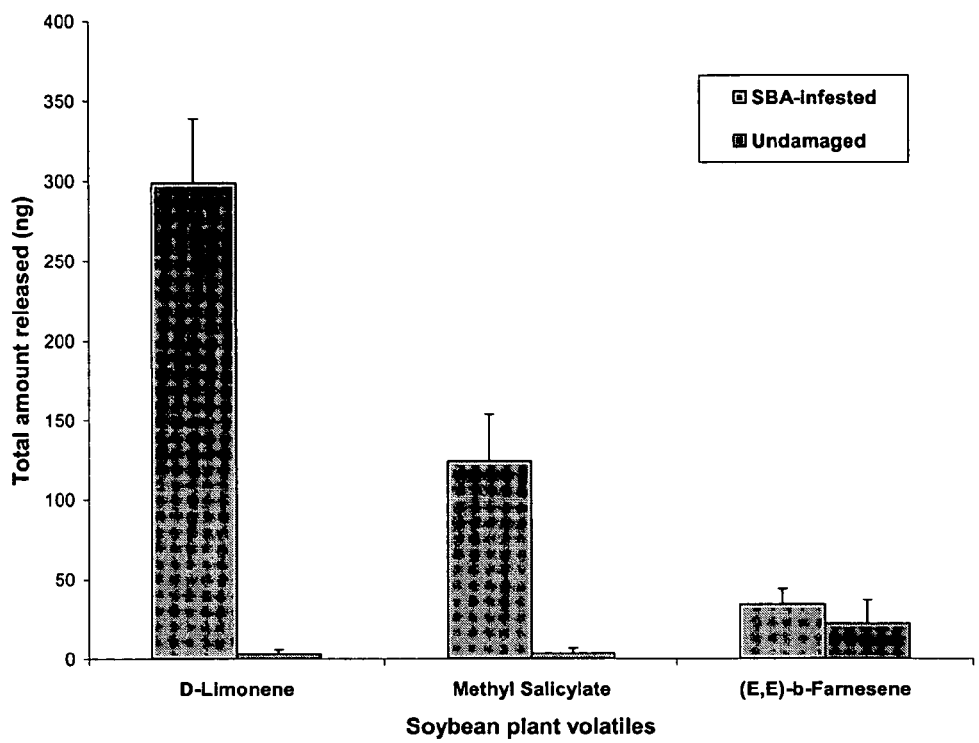
FIG. 6 is two graphs of emission rates of three volatile compounds from plants at first and second vegetative stages of *Glycine max* (V1, upper part and V2, lower part). Asterisks indicate statistically significant differences in volatile release rates between soybean aphid-infested and undamaged plants of *Glycine max* (Student T-test, $n=6$, $P<0.001$).
Figure 6:
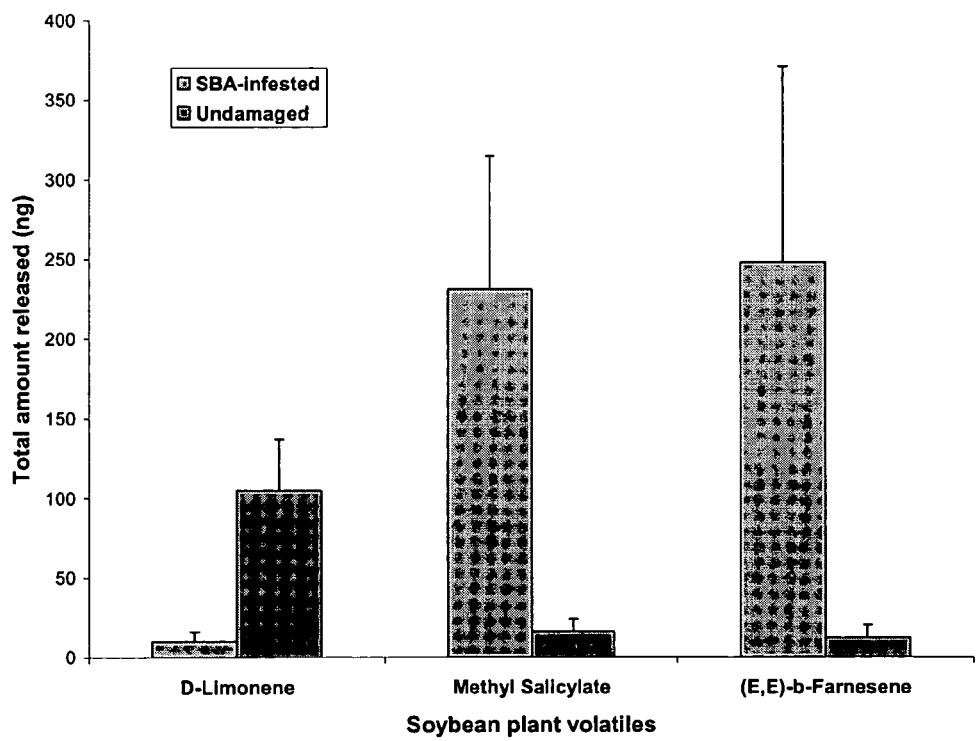
Figure 7:
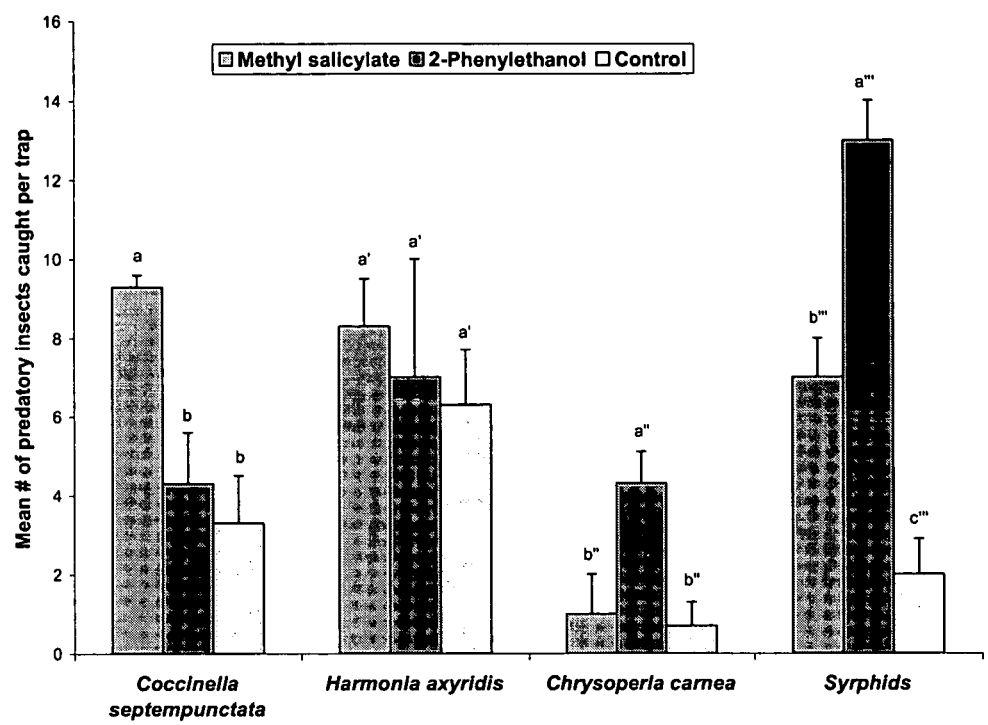
FIG. 7 is a graph of the mean number of predatory insects caught in traps baited with 100 mg of methyl salicylate and 2-phenylethanol, and the control from an Iowa soybean field in 2003. Columns with no letters in common in 4 different categories are significantly different (ANOVA followed by FPLSD test, $P<0.05$).

Volatile compounds from soybean aphid-infested soybean leaf. A total of 21 volatile compounds were tentatively identified from emissions of both infested and uninfested soybean leaves by comparing their retention indices and MS characteristic fragments with those of synthetic standards (FIG. 2). Most volatiles released from the soybean plant were common plant volatiles. Further quantitative analyses from runs of extracts on GC and GC-MS revealed that consistent differences in emissions of D-limonene, methyl salicylate and (E,E)-α-farnesene between the soybean aphid-infested and undamaged soybean plants (FIG. 6). Among these three compounds, methyl salicylate was the only compound emitted significantly higher quantities from soybean aphid-infested soybean plants (both V1 and V2 stage), relative to the undamaged ones. Significantly more amounts of D-limonene and (E,E)-α-farnesene released from the soybean aphid-infested were observed, but differed between the V1 and V2 staged soybean plants.

Figure 3:
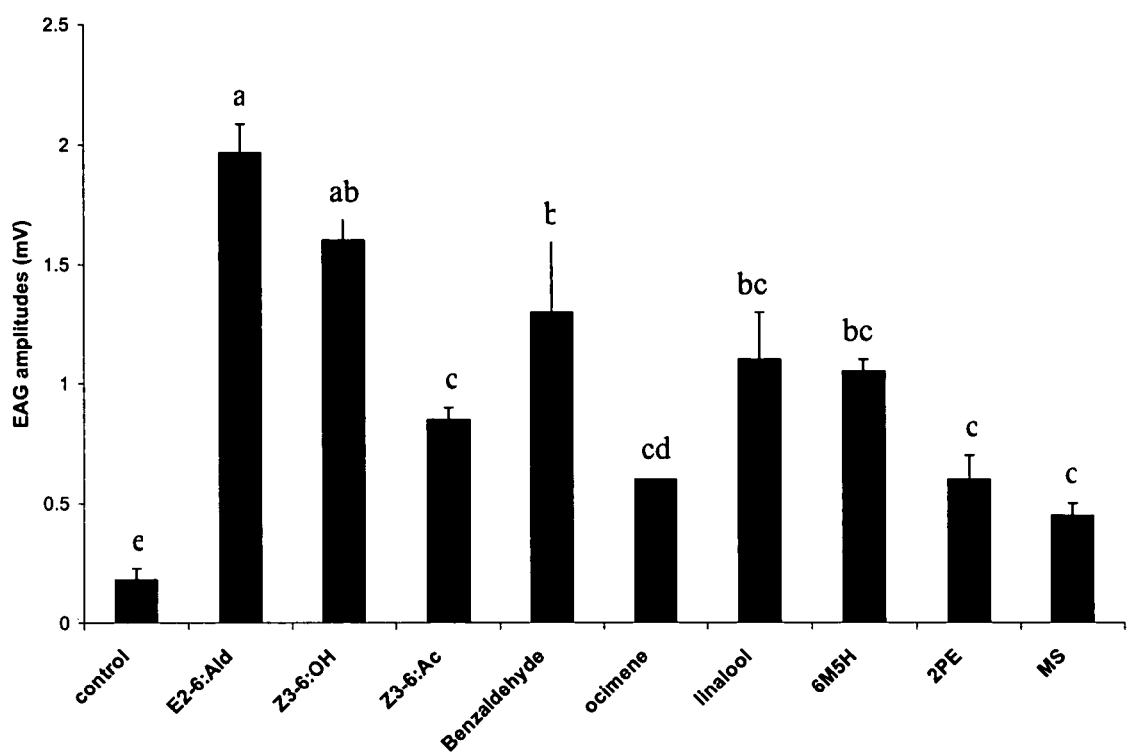
FIG. 3 is a graph of EAG responses of winged soybean aphids, *Aphis glycines*, to some soybean associated volatile compounds. Means (±standard error) with different letters are significantly different (ANOVA followed by FPLSD test, $P<0.001$)
Figure 4:
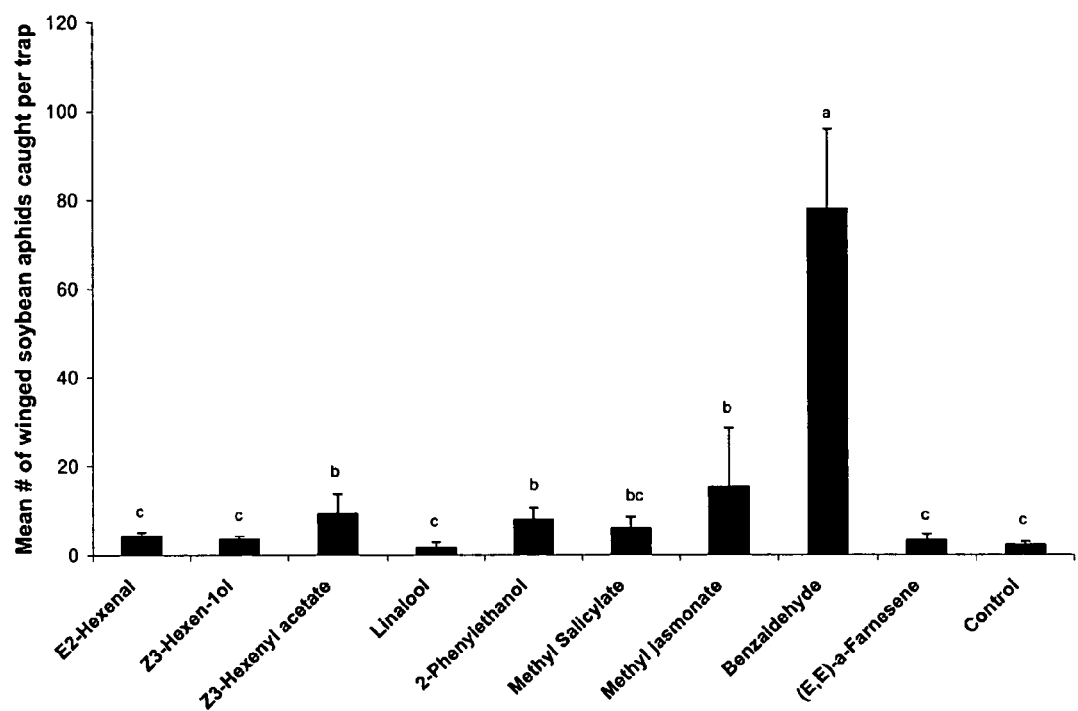
FIG. 4 is a graph of the number of winged soybean aphids caught per trap baited with some selected soybean volatile compounds (synthetic) in the soybean field. Means (±standard error) with different letters are significantly different (ANOVA followed by FPLSD test, $P<0.001$)
Figure 5:
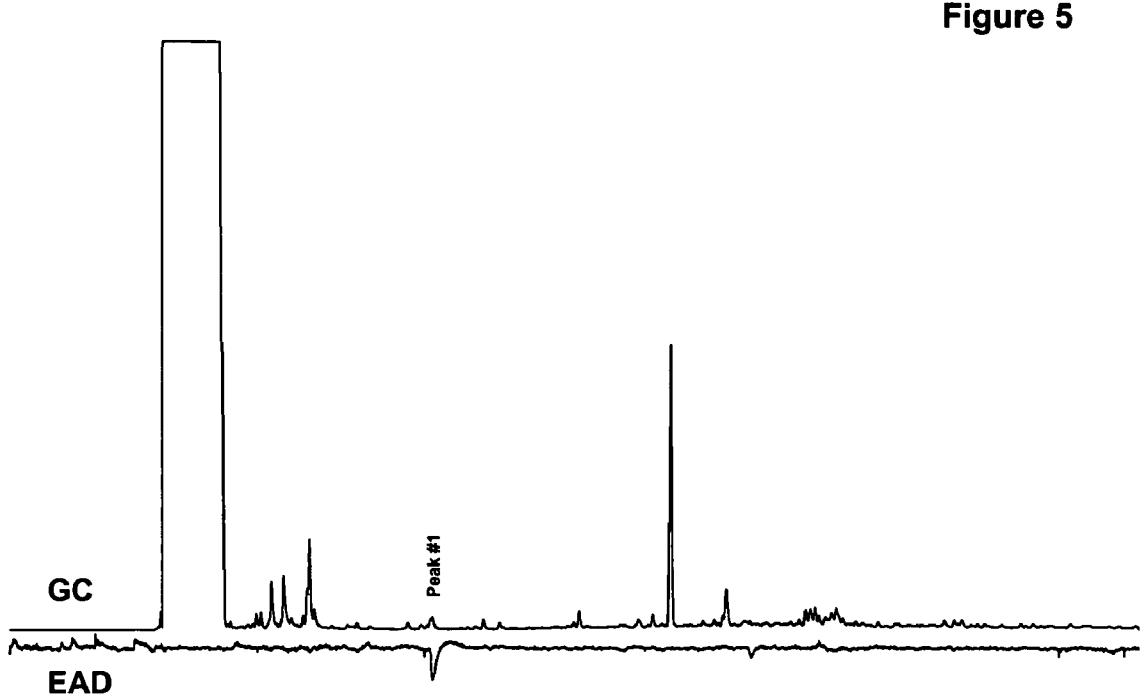
FIG. 5 Shows simultaneously recorded flamed ionization detector (FID) and electroantennographic detector (EAD) responses of antennae of *Coccinella septempunctata* to extracts of soybean aphid-infested plant of *Glycine max*.

EAG responses of soybean aphids to soybean plant volatiles and their attractiveness in the field. Antennae of winged soybean aphids responded strongly to several selected most common soybean associated volatiles, with the highest response to (E)-2 hexenal, and followed by (Z)-3 Hexenol, benzaldehyde, (Z)-3 hexenyl acetate, linalool, 6-methyl-5-hepten-2-one, ocimene, 2-phenylethanol, methyl salicylate, which all significantly stronger than the control (FIG. 3). Field trapping tests showed that winged soybean aphids were caught the most with traps baited with benezaldehyde (FIG. 4). All other compounds elicited EAG responses seemed not to be attractive to winged aphids relative to the control.

Responses of predatory insects to selected attractant compounds in the field trapping tests. Methyl salicylate was significantly attractive to adults of *Coccinella septempunctata*, which is one of dominant predatory lady beetles active during the earlier season, while winged soybean aphids migrated from their overwintering host plants. This compound attracted to some syrphids, but the strongest attraction was observed from 2-phenylethanol. Although similar number of *Harmonia axyridis* was also caught in traps baited with methyl salicylate, but not significantly differed from the control.

Figure 9:
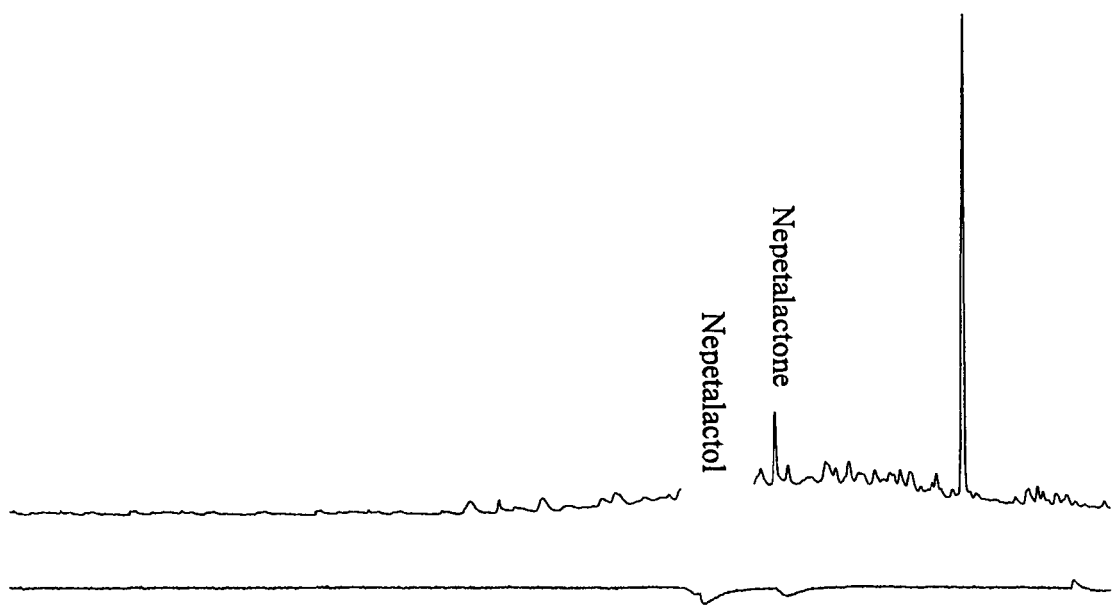
FIG. 9 Shows simultaneously recorded flamed ionization detector (FID) and electroantennographic detector (EAD) responses of male antennae of *Aphis glycines* to two pheromone candidate compounds from extracts of airborne collection of calling female gynoparous soybean aphids.
Figure 10:
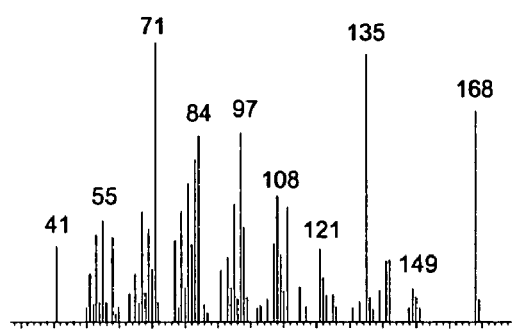
FIG. 10 The upper part shows mass spectra of two pheromone candidate compounds identified from airborne collection of the female soybean aphid. Nepetalactone is at left and nepetalactol is shown at right, which elicited significant EAG active peaks from their conspecific male antennae (FIG. 9). The lower part shows chemical structures of the two pheromone candidate compounds.
Figure 10:
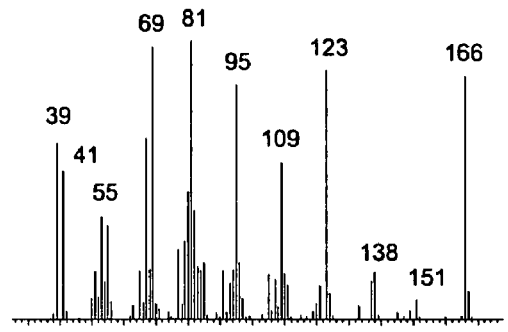
Figure 10:
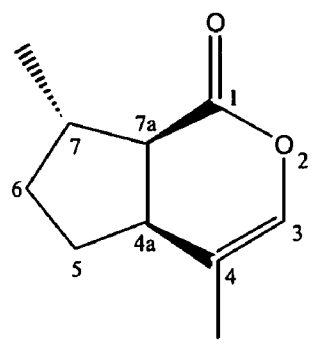
Figure 10:
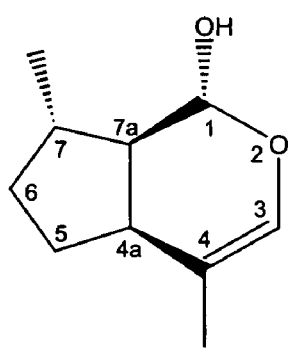

Soybean aphid pheromone identification. The combined GC-Electroantennographic analyses (GC/EAD) of extracts from the airborne collection of calling oviparae on antennae of male soybean aphids have revealed that two EAD peaks were elicited (FIG. 9). The GC-MS analyses of the same extract showed these two peaks with mass spectra (FIG. 10); $1^{st}$ peak: 168 (81), 135 (94), 97 (82), 84 (79), 81 (56), 71 (88), 67 (52), 58 (59), 55 (66), 43 (77), 41 (100); $2^{nd}$ peak 166 (78), 151 (8), 138 (17), 123 (83), 109 (51), 95 (81), 81 (100), 69 (95), 67 (66), 55 (39), 41 (72), 39 (65). The second compound has the same retention time and identical mass spectrum with those of the monoterpene (4aS,7S,7aR)-nepetalactone, identified from the catmint plant, *Nepata cataria*. The mass spectrum of the first peak resembles iridodial with $M_r$ 168 and was similar to one of the (4aS,7S,7aR)-nepetalactol which has been reported as a pheromone compound from another aphid species, *Megoura viciae*. The $^1$H NMR data for peak 2 were in agreement with those of the natural nepetalactone, (4aS,7S,7aR)-nepetalactone. The stereo chemistry of (4aS,7S,7aR)-nepetalactol has been established by $^1$H NMR ($C_6D_6$): characteristic peaks at 6.06 p.p.m. (s, 1H, =CH—O), 4.71 (d, 1H, O—CH—O) and 3.18 (s, br, 1H, OH), with 6.05 Hz couplings from the 4.78 peak to the octet peak at 1.89 (H-7a). The 6.05 Hz coupling between Hs 1 and 7a in the $^1$H NMR spectrum is not sufficient to determine unequivocally the absolute stereochemistry at C-1, but it was claimed as (1R,4aS,7S,7aR)-nepetalactol by X-ray crystallography of the 3,5-dinitrobenzoate of DIBAL-H reduction product obtained from (4aS,7S,7aR)-nepetalactone (Dawson, G. W., et al., 1987 and Dawson, G. W., et al., 1996). Based on the results from GC-MS and NMR analyses, we have confirmed identification of chemical structures of two soybean aphid pheromone components, and their structures are illustrated in FIG. 10.

A comparison test was conducted on pheromone titers and blend ratios of oviparous soybean aphids from a laboratory induced colony as well as those collected from buckthorn leaves in the field. The results (Table 2) have shown that there are no differences in pheromone amount released and blend ratio emitted from naturally occurring females compared to our laboratory induced ones. These results have further demonstrated the reliability of using our laboratory induced oviparous soybean aphids for pheromone characterization, which will be used for the development of mating disruption and mass trapping technology.

TABLE 2

Comparisons of pheromone titers and blend ratios between oviparae of the laboratory-induced and field collected soybean aphids (SBA)

| SBA sources | Pheromone titers (ng/hr/oviparae) | | Pheromone ratios (%) | |
|---|---|---|---|---|
| | Nepetalactol | Nepetalactone | Nepetalactol | Nepetalactone |
| Lab-induced | 0.38 ± 0.13 | 0.82 ± 0.27 | 32 ± 0.7 | 68 ± 0.6 |
| Field-collected | 0.59 ± 0.03 | 1.14 ± 0.06 | 34 ± 0.2 | 66 ± 0.2 |

Data based on analyses of extracts of female pheromone-producing SBA either from laboratory induced colony, or collected from their winter host plants, buckthorns, in Ames, Iowa. For laboratory induced colony, pheromones from a total of 106 calling females in three batches were analyzed. About 60 field-collected calling females in two batches were extracted.

Figure 11:
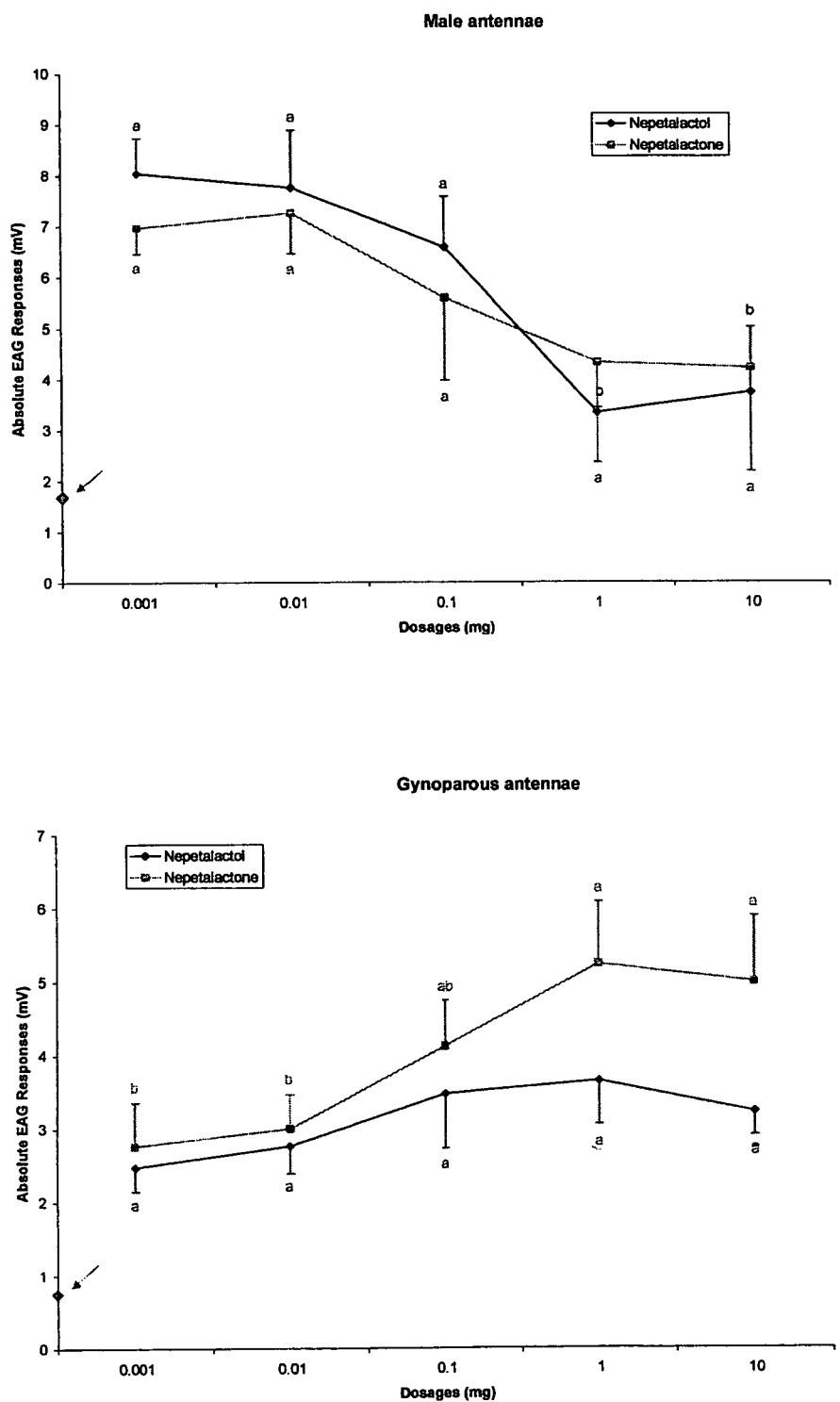
FIG. 11 is two graphs of EAG dose-response curves from male (upper part) and gynoparous female antennae (lower part) of soybean aphids to synthetic pheromone candidate compounds ($n=4$; different letters within a series indicate significant differences, ANOVA followed by FPLSD test, $P<0.05$)

EAG dose-responses of male and gynoparous soybean aphids to the identified sex pheromone compounds. The present electroantennographic (EAG) analyses on the antennae of both types of soybean aphids have revealed the presence of olfactory receptors tuned to the identified pheromone compounds with different response profiles (FIG. 11). Male antennae are highly sensitive to the two pheromone compounds at relatively lower dosages, with the response decreasing significantly when the dose exceeded 1 mg. These findings suggest that sensory adaptation does occur on male soybean aphids. In contrast, gynoparous female soybean aphid antennae showed a higher EAG response when pheromone exceeded a 1 mg dosage, particularly in the case of nepetalactone.

Figure 12:
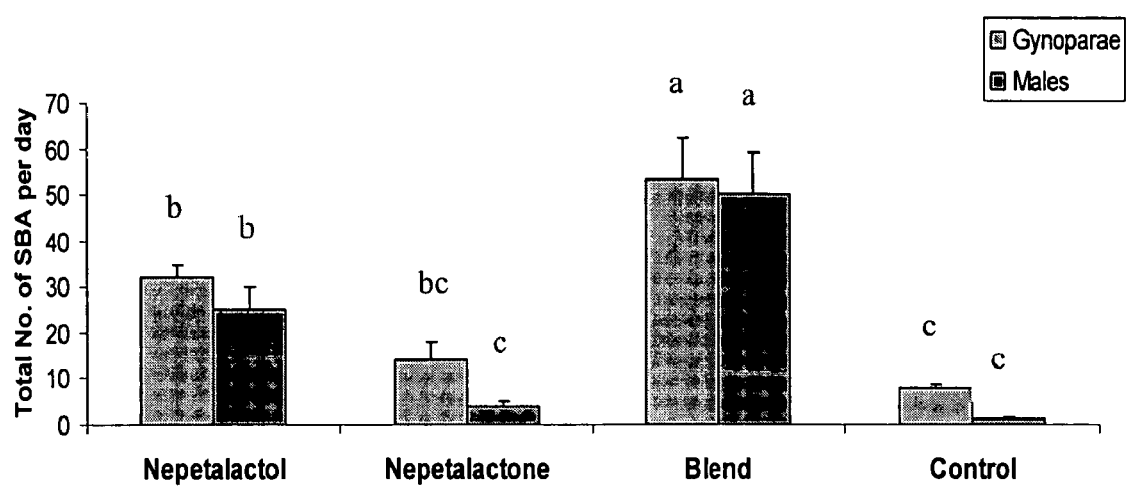
FIG. 12 is a graph of total number of male and gynoparous female soybean aphids caught in traps baited with different combinations of the two pheromone candidate compounds in soybean fields ($n=5$; columns with no letters in common are significantly different, ANOVA followed by FPLSD test, $P<0.05$).
Figure 13:
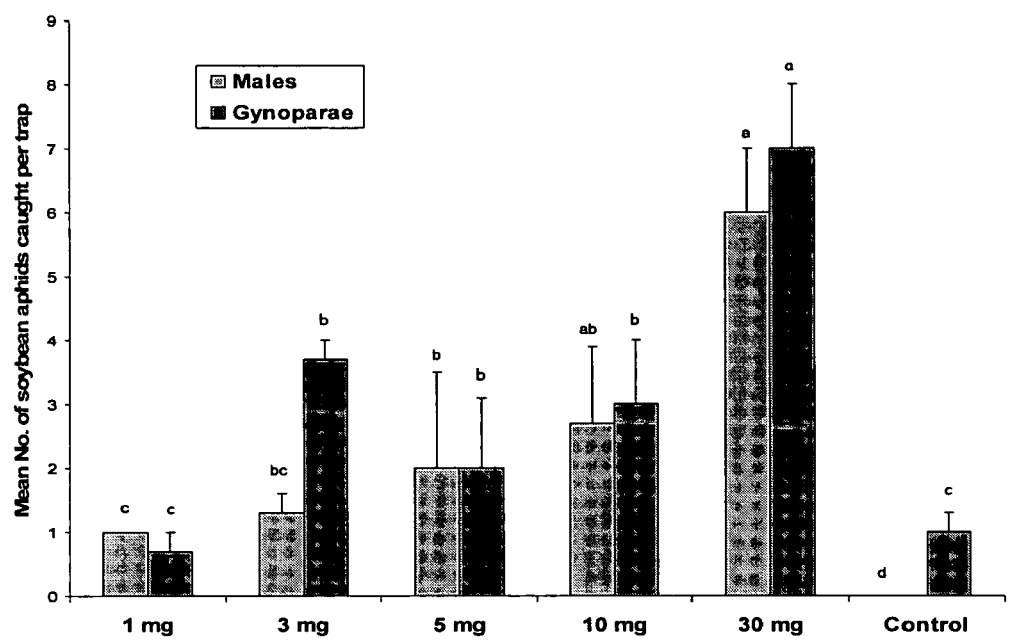
FIG. 13 is a graph of mean number of winged soybean aphids caught in traps baited with different dosages of the blend of pheromone candidate compounds ($n=5$; columns with no letters in common are significantly different, ANOVA followed by FPLSD test, $P<0.05$).
Figure 14:
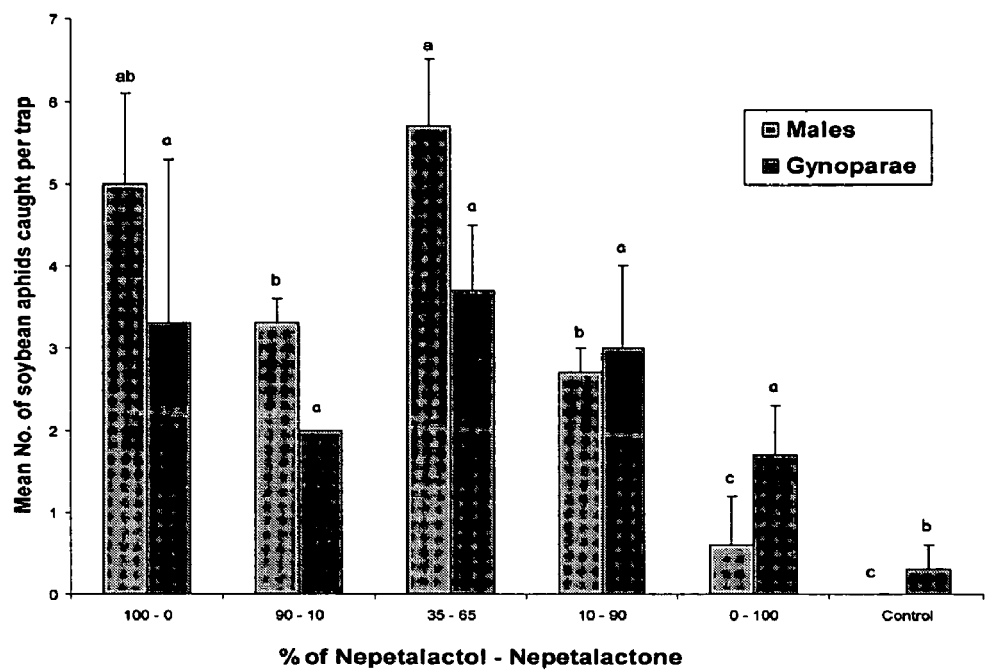
FIG. 14 is a graph of mean number of winged soybean aphids caught in traps baited with different ratios of the two pheromone candidate compounds ($n=5$; columns with no letters in common are significantly different, ANOVA followed by FPLSD test, $P<0.05$).

Field trapping of soybean aphids by synthetic sex pheromone compounds. Field trapping tests conducted in soybean fields using synthetic pheromone lures (10 mg) showed that a blend containing nepetalactol and nepetalactone at a ratio of 35:65 caught the highest number of male and gynoparous soybean aphids (FIG. 12). Significantly lower catches were found compared to traps baited with either nepetalactol or nepetalactone alone. A second field trapping test using different dosages of the most attractive blend was conducted in the same field at a time later in the season showed that traps loaded with 30 mg of pheromone caught the highest number of both types of soybean aphids (FIG. 13). We also tested effects of different amounts of nepetalactol in pheromone lures on the attractiveness to male and gynoparous female soybean aphids. The results showed that the minimum amount of nepetalactol in the blend has to exceed 10%, in order to maintain the attractiveness of the lure to males (FIG. 14). Gynoparous female soybean aphids responded equally well to traps baited with pheromone lures containing no nepetalactol as they did to those with nepetalactol.

Pheromone mass trapping lure and mating disruption dispenser. The soybean aphid sex pheromone lure is comprised of a brown, borosilicate glass vial with a pre-drilled hole at the plastic cap (1 mm diameter), and with a loading of 10-50 mg of synthetic pheromone components at a ratio of 35:65. The mating disruption dispenser is designed based on our EPA-registered MSTRS® pheromone disruption dispensers (bags) (www.mstrs.com), in which pheromone components were formulated inside a modified MSTRS® bag having UV/photo-protected membranes. The working mechanisms of the current two systems are that the soybean aphid pheromone release rates are controlled by using different loading (pheromone lure) and permeability of the plastic membranes comprising the bags' outer envelope (mating disruption dispenser). Our targeted emission rate for mass trapping lure is 100 ng/hr (for 30 days) and for mating disruption dispenser is 1.0 μg/min (for 30 days). Soybean aphid mass trapping pheromone lure (in a water trap) and mating disruption dispenser were tested on soybean aphid winter host plant, the buckthorn. Table 3 and 4 show its release rates through a 30-day period.

TABLE 3

Release rates of a 10 mg soybean aphid pheromone mass trapping dispenser during a 4-week period

| Duration | Pheromone released (ng/hr) Mean ± Std. Error | |
|---|---|---|
| | Nepetalactol | Nepetalactone |
| $1^{st}$ Day | 734 ± 39 | 1373 ± 256 |
| End of $1^{st}$ week | 273 ± 39 | 982 ± 123 |
| End of $2^{nd}$ week | 152 ± 91 | 630 ± 286 |
| End of $3^{rd}$ week | 120 ± 32 | 373 ± 113 |
| End of $4^{th}$ week | 109 ± 19 | 139 ± 17 |

Data based on three analyses of Super Q extracts from airborne collections of soybean aphid pheromone dispensers which were hang in the middle of a 200 ml glass collecting device (23 ± 2° C., 50% humidity, the flow rate at 100 ml/min).

TABLE 4

Release rates of soybean aphid pheromone mating disruption dispensers

| Time | Total Pheromone released (μg/min) Mean ± Std. Err. |
|---|---|
| $1^{st}$ Day | 13.04 ± 0.54 |
| End of $1^{st}$ week | 4.49 ± 1.40 |
| End of $2^{nd}$ week | 1.69 ± 0.23 |
| End of $3^{rd}$ week | 1.55 ± 0.49 |
| End of $4^{th}$ week | 0.79 ± 0.26 |

Data based on three analyses of TENAX extracts from airborne collections of soybean aphid pheromone mating disruption dispensers in a closed collecting system in the fume hood (23 ± 2° C., 50% humidity). The flow rate was maintained at 750 ml/min, and each collection lasted 10 min. After collection, dispensers were set in the soybean field.

Figure 15:
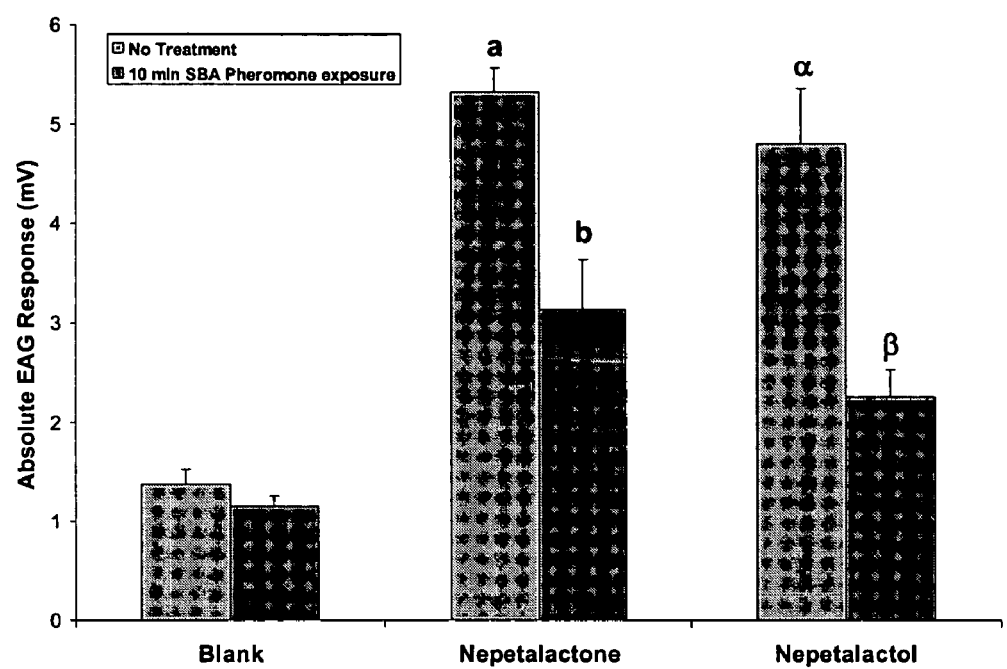
FIG. 15 is a graph of EAG response amplitudes of males and gynoparae of soybean aphids, with or without pre-exposure to pheromone disruption dispensers (10 min), to puffs of aphid pheromone compounds loaded at 10 μg in odor cartridges. Different letters on top of bars indicate significant differences (Student T-test, $P<0.05$).

EAG responses of pheromone-pre-exposed soybean aphids We have pre-exposed males and gynoparae of soybean aphids to the pheromone mating disruption dispenser for 10 min, then tested their EAG responses to both components. The results show that significantly lower EAG responses were elicited from antennae of pre-exposed soybean aphids than to those that were not pre-exposed (FIG. 15). These findings suggest that sensory adaptation does occur on both male and gynoparous female soybean aphids, possibly reducing attraction of aphids and increasing the chances for disrupting males' mate-finding success and gynoparae's ability to locate their host plant habitat by cueing in on pheromones.

Figure 16:
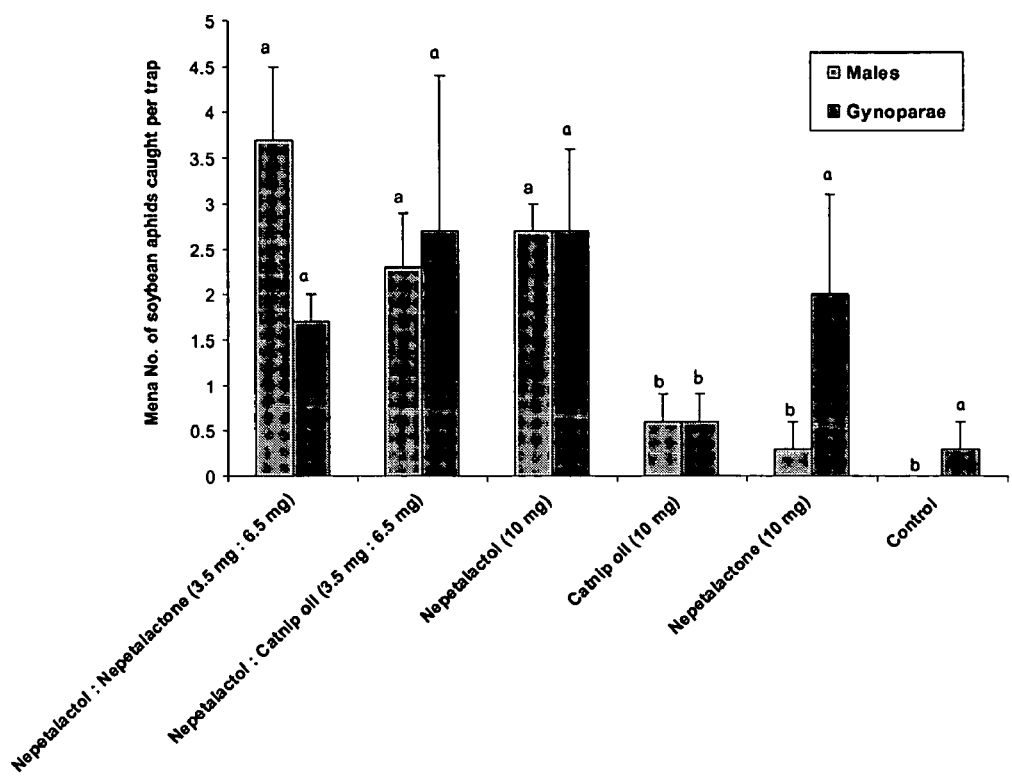
FIG. 16 is a graph of mean number of winged soybean aphids caught in water traps baited with different combinations of catnip oil and the two pheromone compounds ($n=5$, columns with no letters in common are significant different, ANOVA followed by FPLSD test, $P<0.05$)

Cost-Effectiveness Tests: One of the most important factors for successfully developing these products will be a low cost and high effectiveness of the active ingredient (the pheromone). In order to reduce the cost, we experimented with using as little pheromones as possible, while maintaining an optimal level of attraction needed for either trapping soybean aphids or disrupting their mate finding. Results from field tests on effects of different loadings of the two pheromone components on pheromone dispensers' attractiveness showed that to achieve optimal attraction the minimum amount of nepetalactol needed is about 10% (FIG. 14). We conducted another field experiment to see whether it is possible to use the catnip oil (the starting material for mass-producing the soybean aphid pheromone), instead of purified nepetalactone. The results have shown that the traps baited with catnip oil (a replacement of nepetalactone) are as attractive as those either using the synthetic blend or synthesized 10 mg of nepetalactol (FIG. 16). In addition, we formulated our mating disruption dispensers with three different loadings of nepetalactol, 15%, 23%, and 50%, respectively. The results of release rates from these three dispensers are displayed in Table 5.

TABLE 5

Release rates of soybean aphid pheromone mating disruption dispensers with different loadings of Nepetalactol

| | Total Pheromone released (μg/min) (Mean ± Std. Err.) Nepetalactol | | |
|---|---|---|---|
| Time | 50% | 23% | 15% |
| $1^{st}$ Day | 34.31 ± 3.24 | 31.11 ± 5.37 | 17.5 ± 2.15 |
| $1^{st}$ week | 18.61 ± 7.94 | 18.31 ± 2.41 | 8.37 ± 3.7 |
| $2^{nd}$ week | 0.95 ± 0.09 | 0.91 ± 0.06 | 0.8 ± 0.08 |
| $3^{rd}$ week | 0.95 ± 0.29 | 0.65 ± 0.13 | 0.6 ± 0.2 |

Data based on three analyses of TENAX extracts from airborne collections of soybean aphid pheromone mating disruption dispensers in a closed collecting system in the fume hood (23 ± 2° C., 50% humidity). The flow rate was maintained at 750 ml/min, and each collection lasted 10 min. After collection, dispensers were set in the soybean field.

Figure 8:
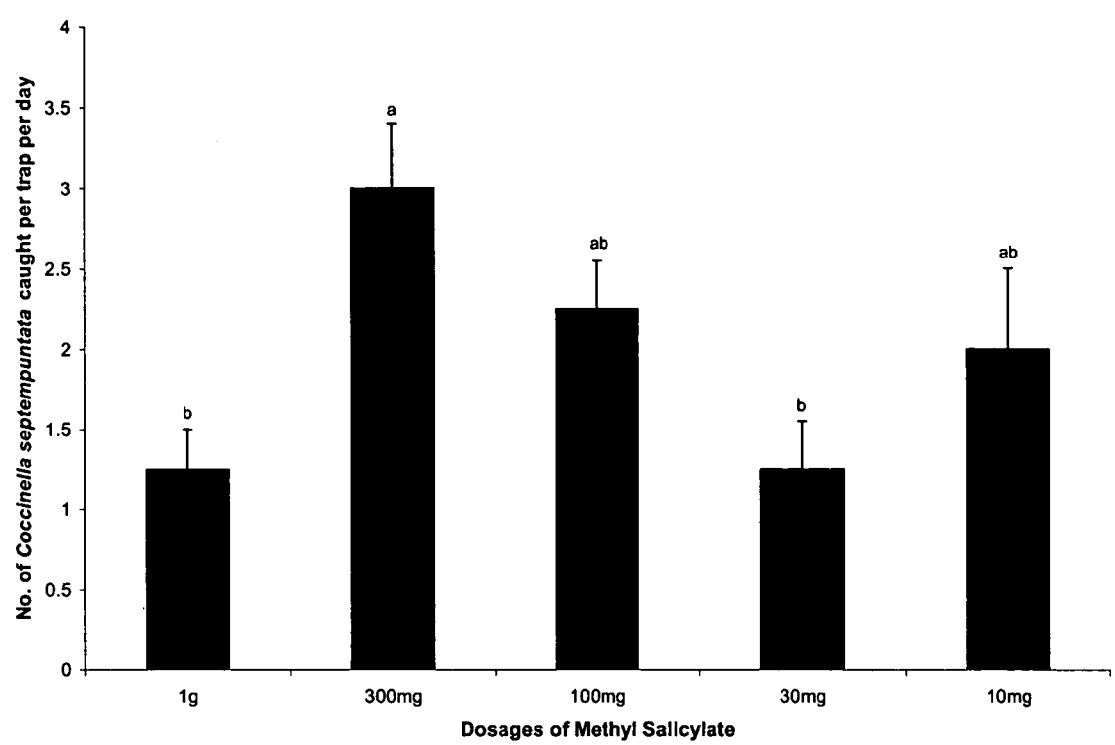
FIG. 8 is a graph of the mean number of *Coccinella septempunctata* caught in traps baited with different doses of methyl salicylate from an Iowa soybean field in 2004. Columns with no letters in common are significantly different (ANOVA followed by FPLSD test, $P<0.05$).
Figure 17:
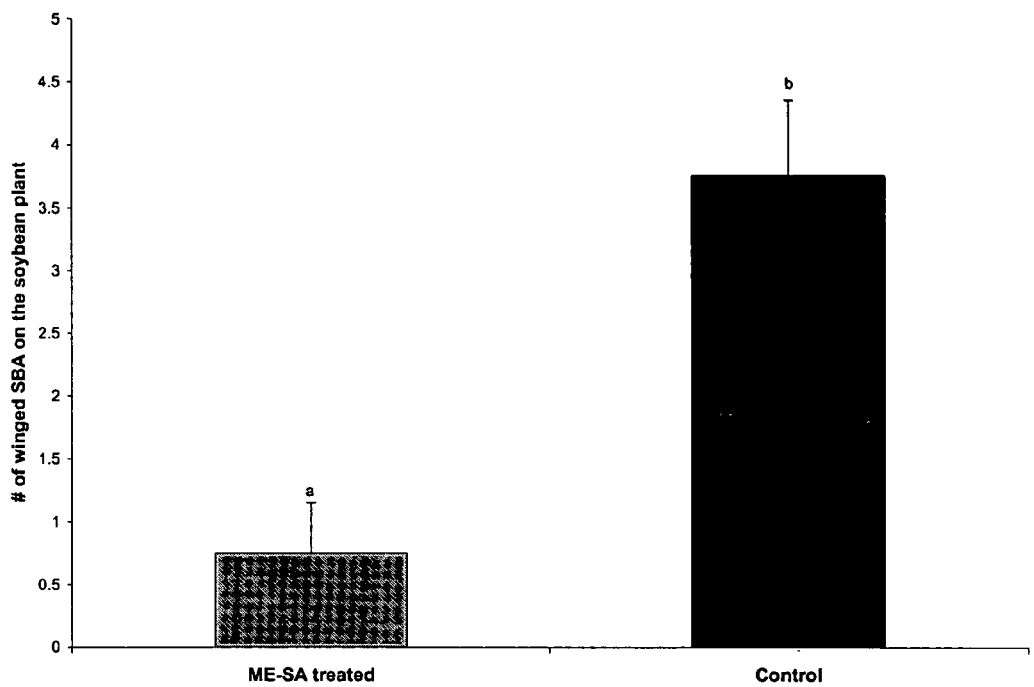
FIG. 17 is two graphs; the upper part shows mean number of winged soybean aphids found on potted soybean plants with or without treated with methyl salicylate (impregnated at 100 mg on cotton rolls); and the lower part shows their effect on soybean aphid growth.
Figure 17:
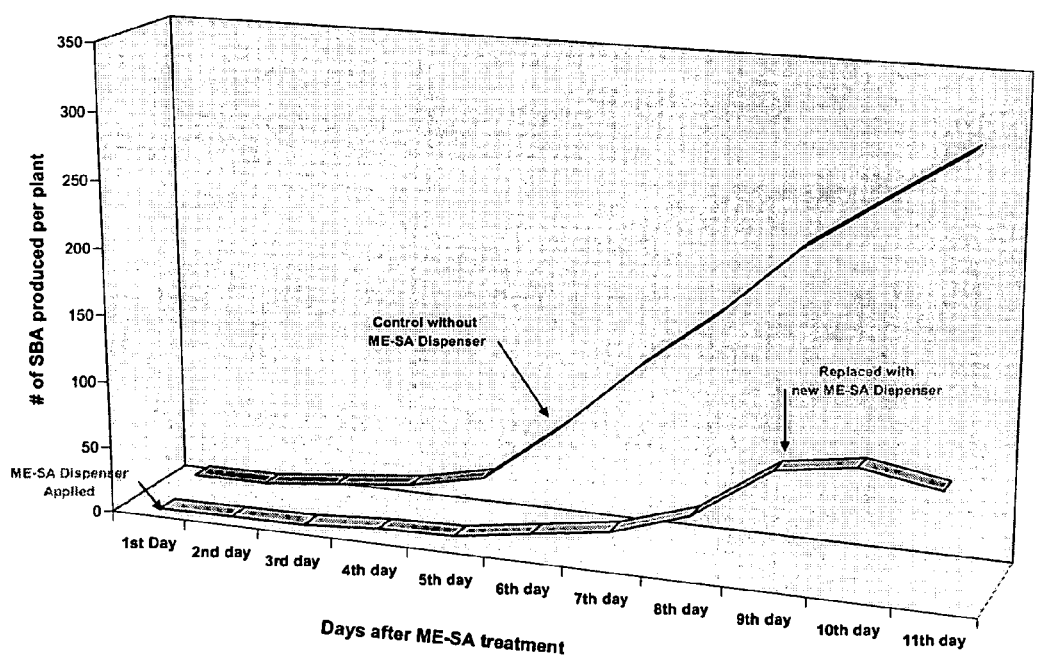

Suppressing soybean aphid growth by methyl salicylate: A dose response test of methyl salicylate to *Coccinella septempunctata* showed that a effective dosages ranging from 10 mg to 300 mg loading into the attractant lure (FIG. 8). This identified soybean aphid-induced plant defensive volatile can also act as repellent for inhibiting soybean aphid growth. The caged experiment with soybean plants treated with methyl salicylate showed that the application of this compound significantly reducing the soybean aphid colonizing on soybean plants (FIG. 17, upper); and also this compound suppress the growth of wingless soybean aphids on soybean leaves (FIG. 17, lower part). The use of this compound obviously has double benefits for soybean aphid control. A controlled-release plastic sachets containing 4 g of methyl salicylate is formulated using double-layer polyethylene sheets, and the release rates are adjusted from 36 mg/day (1st week); 29 mg/day (2nd week); 3.5 mg/day ($3^{rd}$ week) and 1.2 mg/day ($4^{th}$ week).

Figure 18:
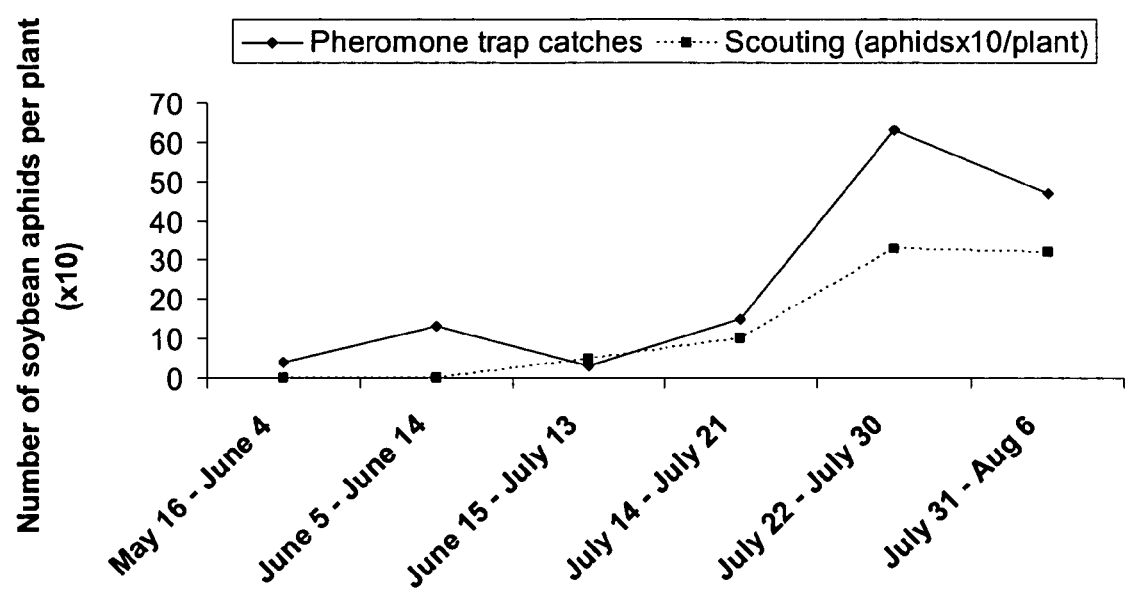
FIG. 18 is a graph of comparisons between numbers of alate soybean aphids captured in pheromone traps and the numbers of apterous females found on leaves during standard scouting sample procedures in a 5-acre soybean field in Decorah, Iowa, 2004.

The Correlation between the trapping catches and the field scouting data of soybean aphid number on soybean leaves: We have demonstrated that strong EAG responses from antennae of spring alate soybean aphids (the overwintering generation that starts building colonies on soybeans) to the two synthetic pheromone components and some soybean associated volatiles. Further field experiments from June to August in 2004 showed that the catches of winged females from the traps correlated well with the abundance of wingless spring alate aphid numbers in the field (FIG. 18).

REFERENCES

Anderson, M. and Bromley, A. K. 1987. Sensory system, pp. 153-162. in "*Aphids: their biology, natural enemies, and control*" edited by A. K. Minks and P. Harrewijn. Amsterdam. Elsevier.

Baker, T. C., and Heath, J. J. (2004) Pheromones—function and use in insect control. In: *Molecular Insect Science*. L I Gilbert, K Iatro, S S Gill eds) Elsevier. Volume 6, pp. 407-460.

Baker, T. C., R. T. Staten and H. M. Flint. 1990. Use of pink bollworm pheromone in the southwestern United States. In "Behavior-Modifying Chemicals for Insect Management," R. Ridgway, R. M. Silverstein and May Inscoe (eds.). Marcel Dekker, Inc., New York, pp. 417-436.

Baker, T. C., Mafra-Neto, A., Dittl, T., and Rice, M. E. 1997. A novel controlled-release device for disrupting sex pheromone communication in moths, pp. 141-149. in Technology transfer in mating disruption, Eds. P. Witzgall and H. Arm. IOBC wprs Bulletin, vol. 20, Montpellier, France.

Baker, T. C., H. Y. Fadamiro, and A. A. Cossé. 1998. Widely-spaced, high-emission-rate pheromone sources suppress mating of European corn borer females. In. Zalucki, M. P., R. A. I. Drew, and G. G. White (eds.) Pest Management, Future Challenges. Proc. Sixth Australasian Applied Entomological Research Conference. University of Queensland Printery. pp. 279-288.

Boo, K. S., Choi, M. Y., Chung, I. B., Eastop, V. F., Pickett, J. A., Wadhams, L. J. and Woodcock, C. M. 2000. Sex pheromone of the peach aphid, *Tuberocephalus momonis*, and optimal blends for trapping males and females in the field. *J. Chem. Ecol.* 26:601-609.

Campbell C. A. M., Dawson, G. W., Griffiths, D. C., Pettersson, J., Pickett, J. A., Wadhams, L. J., and Woodcock C. M. 1990. Sex attractant pheromone of damson-hop aphid Phorodon humuli (Homoptera, aphididae). *J. Chem. Ecol.* 16:3455-3465.

CANARD, M., SÉMÉRIA, Y., and NEW, T. R. 1984. Biology of Chrysopidae, pp. 294, DR W. JUNK Publishers, The Hague/Boston/Lancaster.

Chicago Tribune—Knight Ridder/Tribune Business News. 2003. Soybean aphids drain production of Midwestern cash crops. Oct. 11. 2003.

CNN News (Associated Press). 2003. Aphids whittling soybean farmers' profits. Nov. 25, 2003.

Cullen, E. 2004. Soybean aphid-Wisconsin 2003 Recap. Midwest States Soybean Aphid Management Workshop, Feb. 5, 2004.

Du, Y-J., Yan F-S., Han X-L., and Zhang G-X. 1995. Olfaction in host selection of the soybean aphid *Aphis Glycine*. Acata. Entomol. Sinica. 37:385-391.

Eisenbach, J. And Mittler, T. E. 1980. An aphid circadian rhythm: factors affecting the release of sex pheromone by oviparae of the greenbug, *Schizaphis graminum*. *J. Insect Physiol.* 26:511-515.

FRAZIER, B. D. 1988. Coccinellidae. in Aphids-Their Biology, Natural Enemies and Control. (A. K. Minks, P. Harrewijn, eds.), Vol. B, pp. 231-247. New York, Amsterdam: Elsevier.

GERLING, D. 1990. Natural enemies of white flies: predators and parasitoids. In Whiteflies: Their Bionomics, Pest Status and Management. (D. Gerling, ed.), pp. 147-185. Andover: Intercept Ltd.

Hardie, J., Nottingham, S. F., Dawson, G. W., Harrington, R., Pickett, J. A., and Wadhams, L. J. 1992. Attraction of field-flying aphid males to synthetic sex pheromone. *Chemoecology* 3:113-117.

Hardie, J. Storer, R. J., Cook, F. J., Campbell C. A. M., Wadhams, L. J., Lilley, R., and Peace, L. 1996. Sex pheromone and visual trap interactions in mate location strategies and aggregation by host-alternating aphids in the field. *Physiol. Entomol.* 21:97-106.

Kobayashi, M., Wada, T., Inoue, H. 1981. A comparison of communication disruption technique and mass-trapping technique for controlling moths using sex pheromone of *Spodoptera litura* (F.) (Lepidoptera: Noctuidae). *Proc. Japan/USA Symp. On IPM.*, pp 32-40.

Lösel, P. M., Lindemann, M., Scherkenbeck, J., Maier, J. Engelhard, B., Campbell, C. A. M., Hardie, J., Pickett, J. A., Wadhams, L. J., Elbert, A., and Thielking, G. 1996a. The potential of semiochemicals for control of *Phorodon humuli* (Homoptera: Aphididae). *Pestic. Sci.* 48:293-303.

Lösel, P. M., Lindemann, M., Scherkenbeck, J., B., Campbell, C. A. M., Hardie, J. A., Wadhams, and J., Pickett. 1996b. Effect of primary-host kairomones on the attractiveness of the hop-aphid sex pheromone to *Phorodon humuli*. *Entomol. Exp. Applic.* 80:79-82.

Marsh, D. 1975. Responses of male aphids to the female sex pheromone in *Megoura viciae* Buckton. *J Entomol. Ser.* A 50:43-64.

Midwest States Soybean Aphid Management Workshop, Feb. 5, 2004. Story County Extension Center.

OBRYCKI, J. J. and KRING, T. J. 1998. Predaceous coccinellidae in biological control. *Annu. Rev. Entomol.* 43:295-321.

NEW, T. R. 1975 The biology of Chrysopidae and Hemerobiidae (Neuroptera) with reference to their usage as biocontrol agents: a review. *Trans. R. Entomol. Soc. London.* 127:115-140.

Ostlie, K. 2004. Soybean aphid: Critical info for clone Warfare. Midwest States Soybean Aphid Management Workshop, Feb. 5, 2004

Pettersson, J. 1970. An aphid sex attractant. I. Biological, studies. *Entomol. Scand.* 1:63-73.

Pettersson, J. 1971. An aphid sex attractant. II. Histological, ethological and comparative studies. *Entomol. Scand.* 2:81-93.

Pickett, J. A., Wadhams, L. J., and Woodcock, C. M. 1992. The chemical ecology of aphids. *Annu. Rev. Entomol.* 37:67-90.

RUTLEDGE, C. E., O'NEIL, R. J. FOX, T. B. and LANDIS, D. A. 2004. Soybean aphid predators and their use in IPM. *Annals Ent. Soc. Amer.* (Accepted, in revision at journal).

Sanders, C. J. 1997. Mechanisms of mating disruption in moths, pp. 333-346. in Insect Pheromone Research New Direction. Eds. Cardé, R. T. and Minks, A. K. Chapman & Hall, 1997.

Smit, N. E. J. M., Downham, M. C. A., Laboke, P. O., Hall, D. R., Odongo, B. 2001. Mass-trapping male *Cylas* spp. With sex pheromones: a potential IPM component in sweet potato production in Uganda. *Crop-prot.* 20:643-651.

Soybean aphid match 2005. http://www.planthealth.info/soyaphid.htm

Staten, R. T., El-Lissy, O., and L. Antilla. Successful area-wide program to control pink bollworm by mating disruption. In "Pheromone Research: New Directions" R. T. Cardé and A. K. Minks (eds.) Chapman and Hall, New York. pp. 383-396.

Voegtlin, D. J. and Steffey, K. 2004. The soybean aphid in North America: Background and Biology. Midwest States Soybean Aphid Management Workshop, Feb. 5, 2004

Voegtlin, D. J., O'Neil, R. J., and Graves, W. R. 2004. Tests of suitability of overwintering hosts of *Aphis glycines*: identification of a new host association with *Rhamnus alnifolia* L'Héritier. *Ann. Entomol. Soc. Am.* 97:233-234.

Junwei Zhu, Allard Cossé, John Obrycki, Kyung Saeng Boo and Thomas, C. Baker. 1999. Electroantennogram responses of *Colleomegilla maculata* (Coleoptera: Coccinellidae) and *Chrysoperla carnea* (Neuroptera: Chrysopidae) to semiochemicals associated with their prey and host plant. *J. Chem. Ecol.* 25(5):1163-1177.

Junwei Zhu, J J. Obrycki, S A. Ochieng, T C. Baker, J A. Pickett and D. Smiley. 2005. Prey and habitat location by chemically associated odors in predatory insects: Perspectives in chemical ecology and sensory physiology of lacewings *Naturwissenschaften* (in press)

Junwei Zhu, and Kyechung Park. 2005. Prey and habitat location by chemically associated odors in predatory insects: Perspectives in chemical ecology and sensory physiology of lacewings *J. Chem. Ecol.* (in press)

Junwei Zhu, Aijun Zhang, Kye-Chung Park, Tom Baker, Brian Lang, Russell Jurenka, John J. Obrycki, William R. Graves, J. A. Pickett, D. Smiley, Kamlesh R. Chauhan, and Jerome A. Klun. 2005. Prey and habitat location by chemically associated odors in predatory insects: Perspectives in chemical ecology and sensory physiology of lacewings *J. Chem. Ecol.* (submitted)

Junwei Zhu, Jeremy J. Heath, Brian Lang, Thomas C. Baker, and Derrick N. Exner. 2005. Evidence of Enhanced Biological Control of *Aphis glycines* Matsumura by the Application of Beneficial Insect Attractants in Soybean Aphid-Infested Fields. *Environ. Entomol.* (submitted)

What is claimed is:

1. A method of suppressing population of soybean aphids in soybean plants, comprising applying to a target area a composition comprising at least one semiochemical, wherein said semiochemical causes said soybean aphid or a soybean aphid predator to displace toward the source of the composition, wherein said semiochemical is selected from the group consisting of nepetalactone and nepetalactol such that said soybean aphid population is suppressed.

2. The method of claim 1 comprising applying of about 0.05 mg to about 100 mg of nepetalactone to the target area.

3. The method of claim 1 comprising applying nepetalactol to the target area.

4. The method of claims 2 or 3 comprising applying about 0.1 mg to about 50 mg nepetalactol and nepetalactone to the target area.

5. The method of claim 1 comprising applying a composition comprising nepetalactone to the target area.

6. The method of claim 5 comprising applying a composition comprising at least about 10% vol. nepetalactol.

7. The method of claim 5 comprising applying a composition comprising nepetalactol and nepetalactone at a volume ratio of 35:65.

* * * * *